(12) United States Patent
Donofrio et al.

(10) Patent No.: US 7,883,465 B2
(45) Date of Patent: Feb. 8, 2011

(54) FINGER OPERATED SWITCH FOR CONTROLLING A SURGICAL HANDPIECE

(75) Inventors: William T. Donofrio, Cincinnati, OH (US); Richard M. Harper, Cincinnati, OH (US); Richard F. Schwemberger, Cincinnati, OH (US); Robert P. Gill, Mason, OH (US); Mary E. Schramm, Cincinnati, OH (US); Jason A. Born, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1367 days.

(21) Appl. No.: 10/716,127

(22) Filed: Nov. 17, 2003

(65) Prior Publication Data

US 2004/0230214 A1    Nov. 18, 2004

Related U.S. Application Data

(62) Division of application No. 09/879,319, filed on Jun. 11, 2001, now Pat. No. 6,945,981.

(60) Provisional application No. 60/242,159, filed on Oct. 20, 2000.

(51) Int. Cl.
*A61B 8/00* (2006.01)
(52) U.S. Cl. .................................. 600/437; 128/898
(58) Field of Classification Search .............. 606/107, 606/170, 171, 180, 169, 159, 40, 45; 604/22; 600/437, 438; 128/898; 433/118; 200/13, 200/14, 18, 43.01, 50.01
See application file for complete search history.

(56) References Cited

U.S. PATENT DOCUMENTS 2,917,691 A    12/1959    De Prisco et al.
4,321,530 A    3/1982    Kelly et al.

(Continued)

FOREIGN PATENT DOCUMENTS

GB    2 326 346 A    12/1998

(Continued)

OTHER PUBLICATIONS

European Search Report dated Dec. 1, 2003.

*Primary Examiner*—Michael J Milano
*Assistant Examiner*—Victor X Nguyen

(57) ABSTRACT

According to the invention, a finger-operated switch for activating and operating an ultrasonic surgical handpiece is provided. The power output of the surgical handpiece is responsive and proportional to the pressure applied to the finger-operated switch. The finger-operated switch includes, but not limited to, force sensitive resistors whose resistance is proportional to the force applied by the finger of the human operator of the surgical handpiece, force sensitive capacitors whose capacitance is proportional to the pressure, deflection or compression of the insulation layer between two electrodes or is proportional to the spacing between the two conductive layers, strain gauges mounted underneath or integral to the housing of the surgical handpiece such that the pressure applied thereto results in an output change in the strain gauges, magnets or ferromagnets encased or embedded in an elastomer with a sensor inside the surgical handpiece that detects the field strength of the magnet and monitors changes relative to the force applied to the handpiece housing, and piezo film or piezo ceramic whose charge or voltage is proportional to the force applied.

6 Claims, 19 Drawing Sheets

U.S. PATENT DOCUMENTS

| | | | |
|---|---|---|---|
| 4,979,952 A | 12/1990 | Kubota et al. | |
| 5,001,649 A | 3/1991 | Lo et al. | |
| 5,026,387 A * | 6/1991 | Thomas | 606/169 |
| 5,060,658 A * | 10/1991 | Dejter et al. | 606/566 |
| 5,112,300 A | 5/1992 | Ureche | |
| 5,180,363 A | 1/1993 | Idemoto et al. | |
| 5,383,855 A * | 1/1995 | Nicholson et al. | 604/100.03 |
| 5,400,267 A | 3/1995 | Denen et al. | |
| 5,425,704 A | 6/1995 | Sakurai et al. | |
| 5,449,370 A | 9/1995 | Vaitekunas | |
| 5,499,969 A * | 3/1996 | Beuchat et al. | 604/30 |
| 5,529,580 A * | 6/1996 | Kusunoki et al. | 606/170 |
| 5,630,420 A | 5/1997 | Vaitekunas | |
| 5,707,369 A | 1/1998 | Vaitekunas et al. | |
| 5,733,256 A * | 3/1998 | Costin | 604/22 |
| 5,879,364 A | 3/1999 | Bromfield et al. | |
| 5,968,007 A | 10/1999 | Simon et al. | |
| 6,013,048 A * | 1/2000 | Podany et al. | 604/22 |
| 6,017,354 A | 1/2000 | Culp et al. | |
| 6,019,775 A | 2/2000 | Sakurai | |
| 6,037,724 A | 3/2000 | Buss et al. | |
| 6,053,886 A * | 4/2000 | Holland et al. | 604/22 |
| 6,066,135 A | 5/2000 | Honda | |
| 6,090,123 A * | 7/2000 | Culp et al. | 606/180 |
| 6,252,334 B1 | 6/2001 | Nye et al. | |

FOREIGN PATENT DOCUMENTS

| | | | |
|---|---|---|---|
| JP | 2000-271142 A | 10/2000 | |

* cited by examiner

FIG. 1 _PRIOR ART_
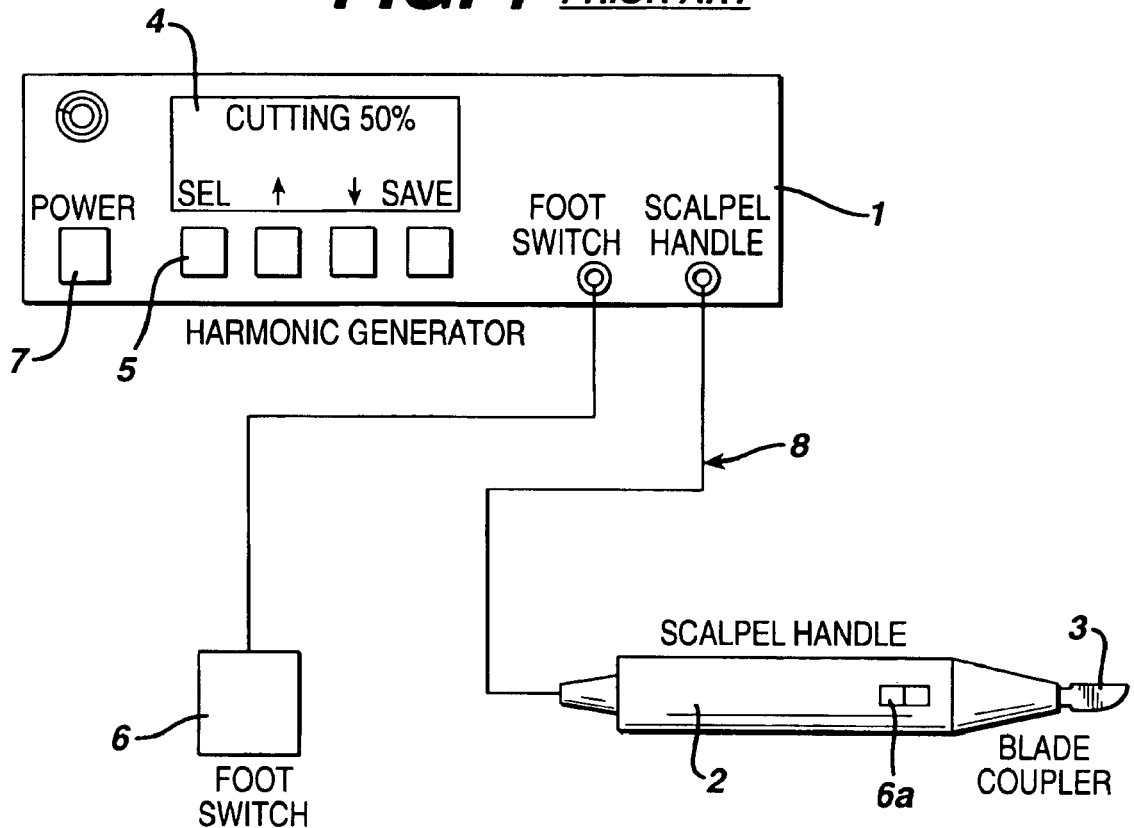
FIG. 1a _PRIOR ART_
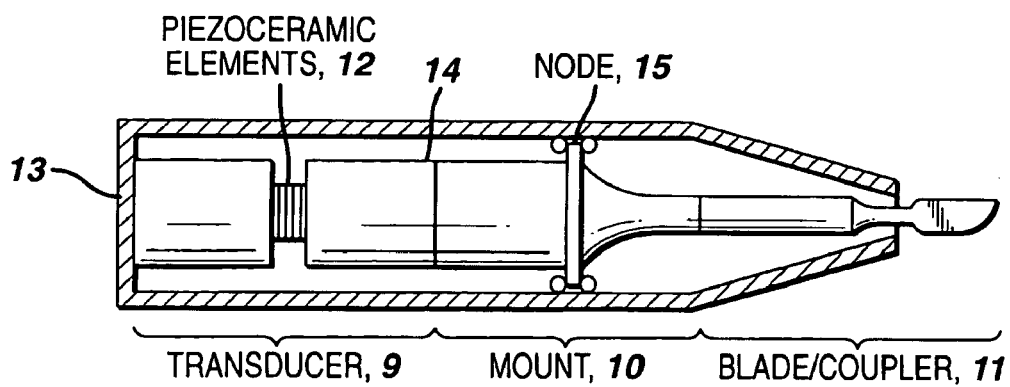

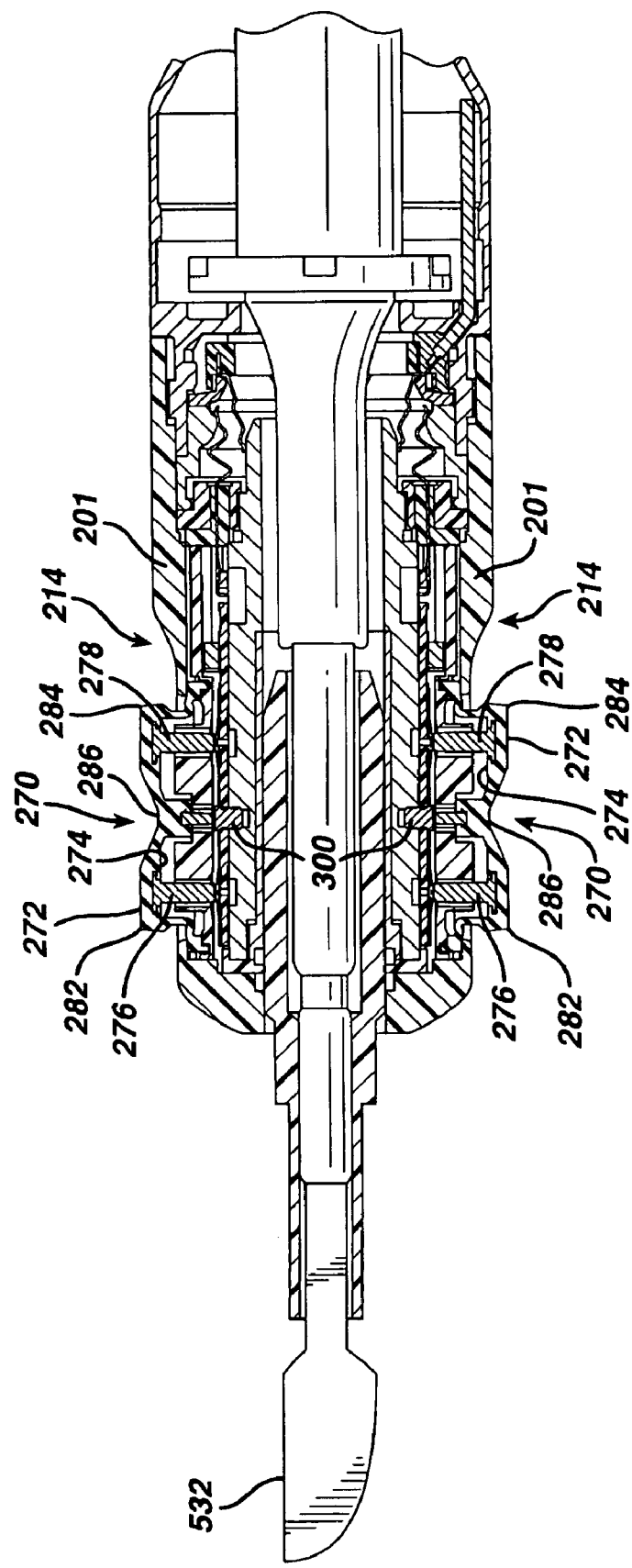

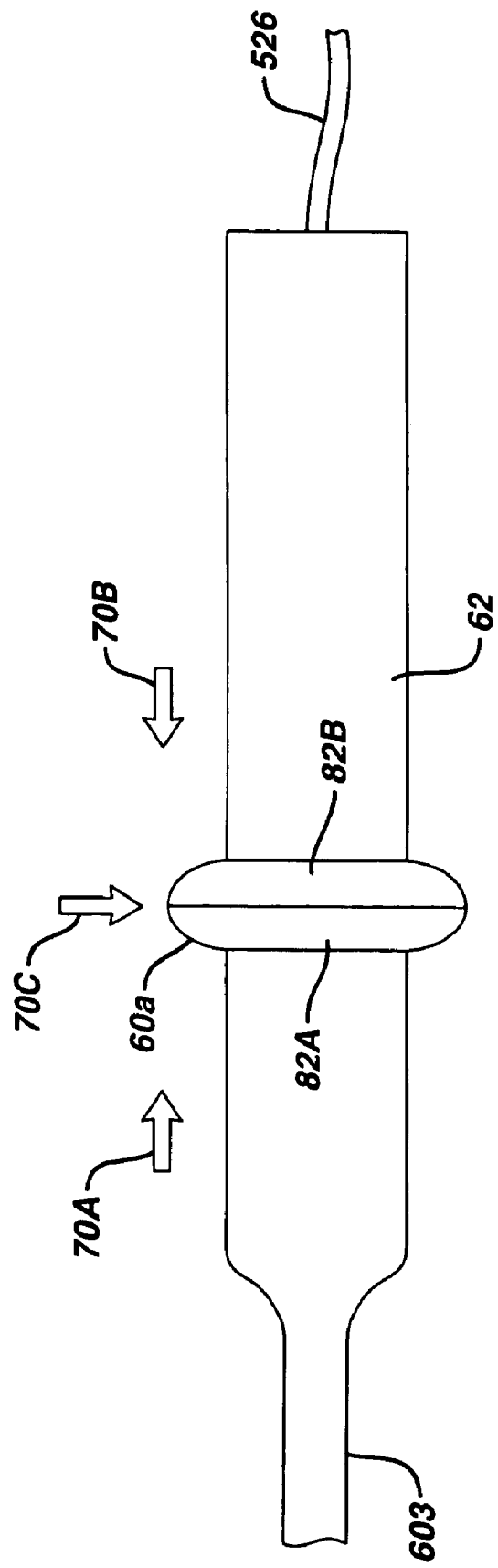

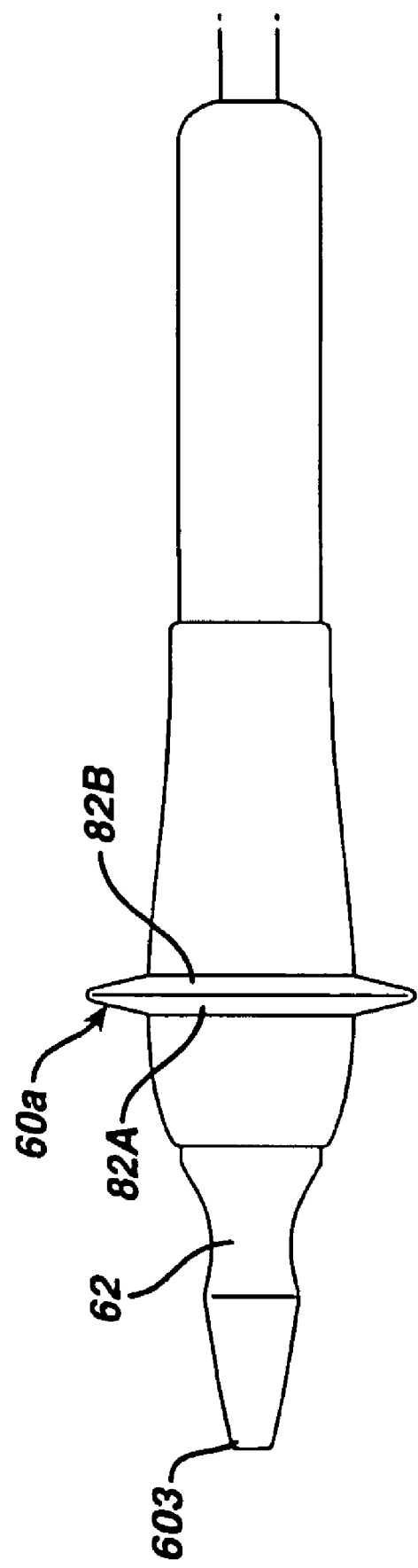

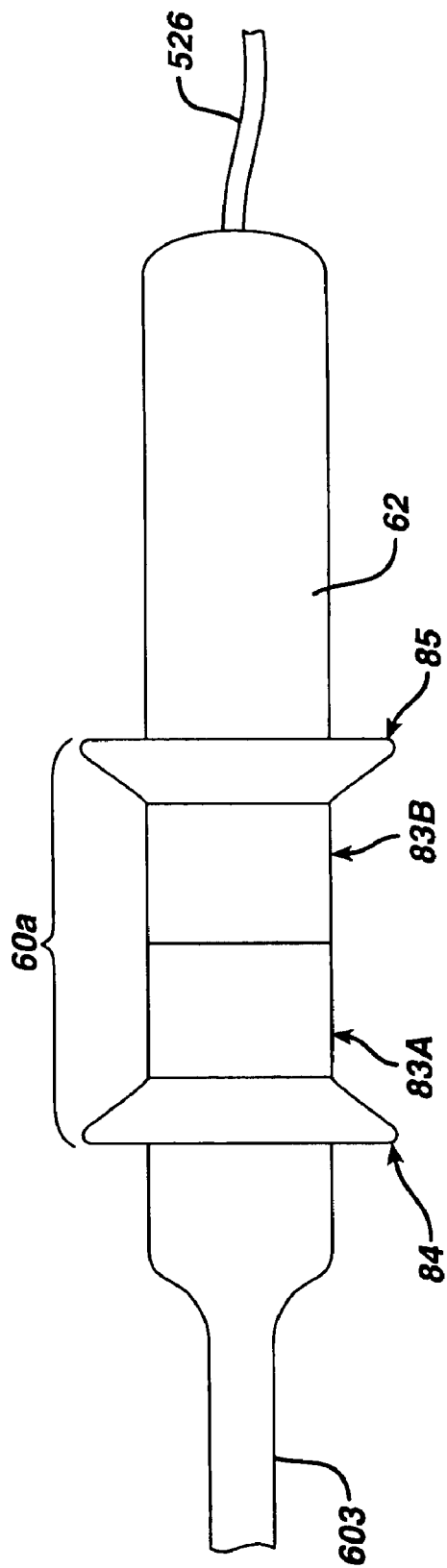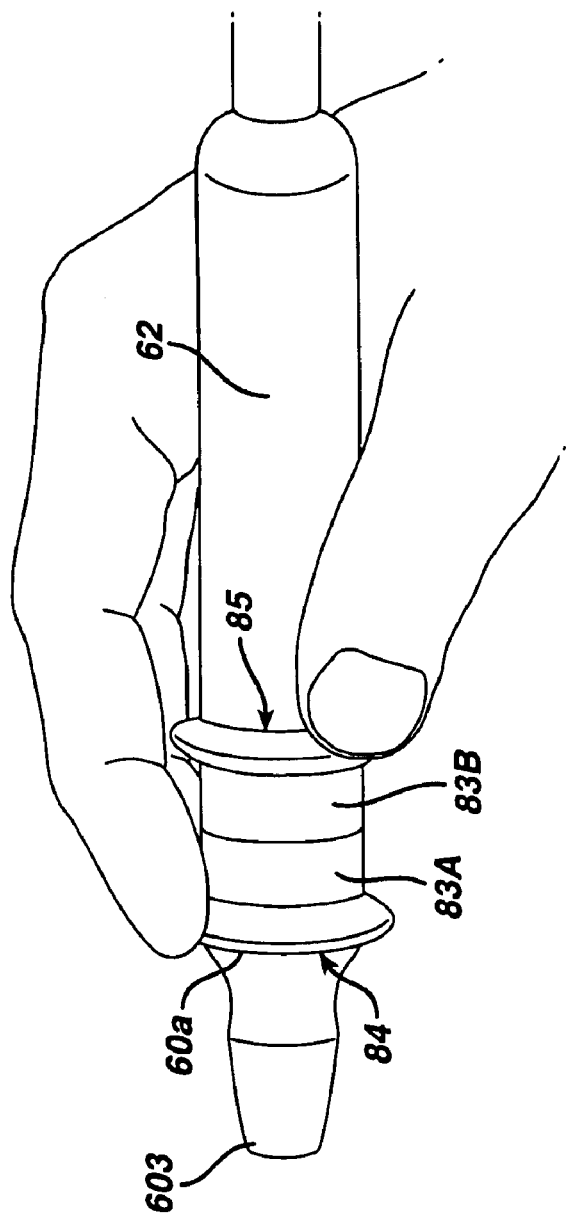

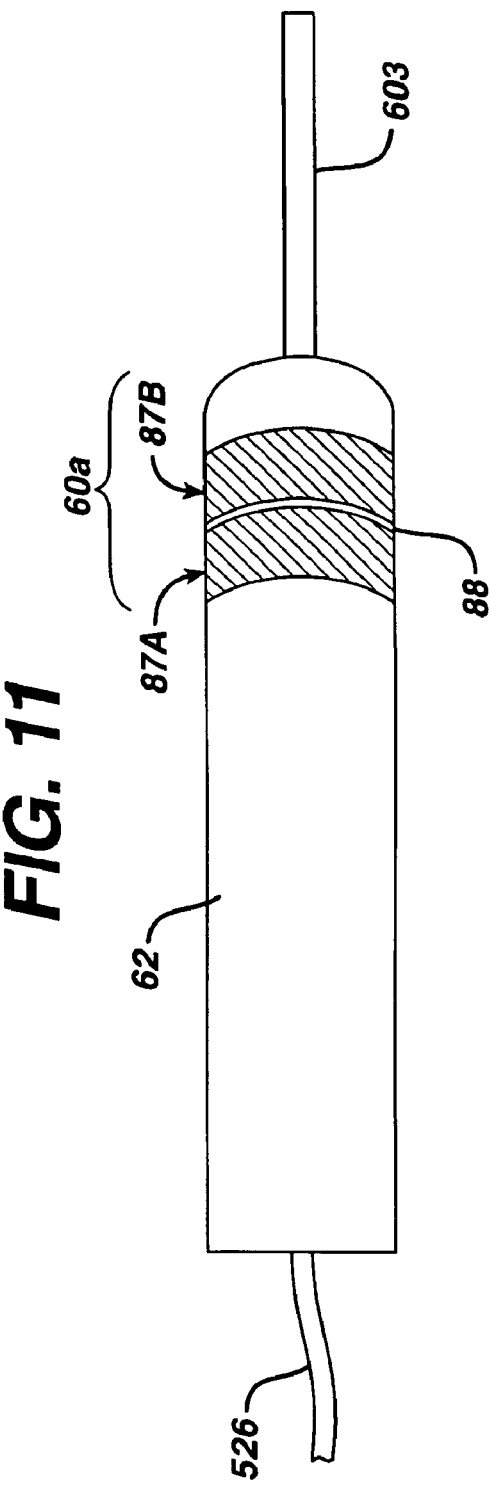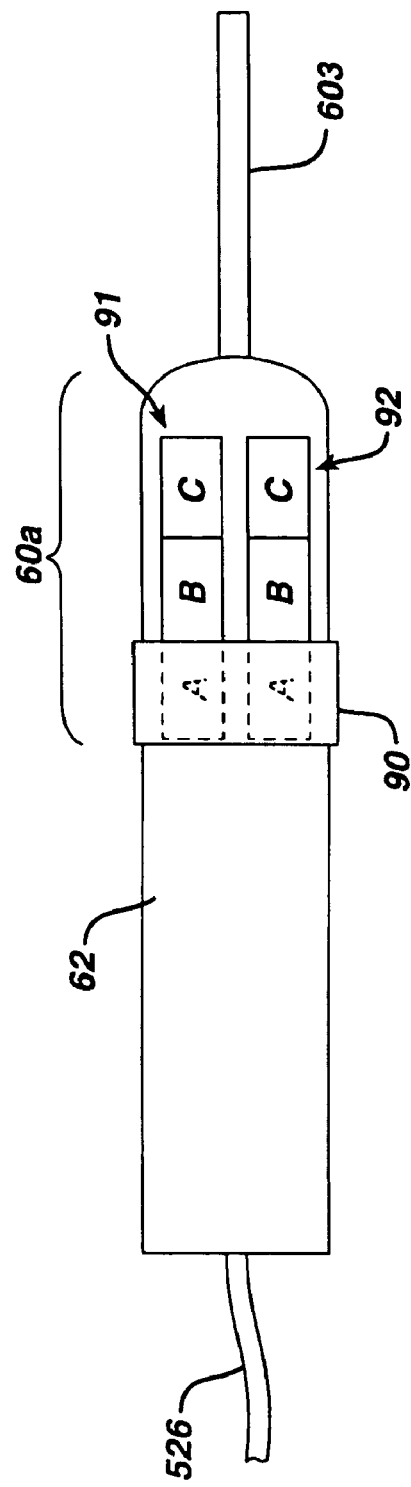

FINGER OPERATED SWITCH FOR CONTROLLING A SURGICAL HANDPIECE

RELATED APPLICATIONS

The present application is a division of application Ser. No. 09/879,319 filed Jun. 11, 2001, now U.S. Pat. No. 6,945,981 which relates to and claims priority of U.S. Provisional Patent Application Ser. No. 60/242,159 filed on Oct. 20, 2000, which are incorporated herein by reference in their entirety.

FIELD OF THE INVENTION

The invention generally relates to the field of medical or surgical instruments and, more particularly, to a novel finger-operated switch for controlling a medical or surgical handpiece.

DESCRIPTION OF THE RELATED ART

Ultrasonic medical or surgical instruments have gained widespread acceptance in the microsurgical field for use in the fragmentation and removal of body tissue. A typical ultrasonic instrument includes an ultrasonic transducer housed in a handpiece. The ultrasonic transducer is operable for converting electrical energy supplied thereto into high-velocity vibrational movements. The transducer-generated ultrasonic vibrations are transmitted to a surgically operative tip (such as a blade or a coagulator) that is coupled thereto.

U.S. Pat. No. 5,026,387 issued to Thomas (the '387 patent), assigned to the assignee of the present application and incorporated herein by reference, describes such an ultrasonic surgical instrument. The ultrasonic instrument according to the '387 patent includes a "power on demand" control feature for causing a surgically sharp cutting instrument, such as a scalpel blade or other surgical instrument (e.g. a dull cautery blade) to automatically shift its operation between an unloaded or idle state and a loaded or cutting state, and vice versa, depending on whether the instrument is in contact with a bodily tissue.

FIG. 1 is a diagram illustrating a typical ultrasonic instrument known in the art in accordance with the '387 patent. As generally shown in FIG. 1, a harmonic generator 1 provides electrical energy to the handpiece 2 that imparts ultrasonic longitudinal movement to a surgical device, such as a sharp scalpel blade 3 that is used for dissection and/or coagulation. The harmonic generator 1 includes a liquid crystal display device 4 indicating, e.g., the selected cutting power level as a percentage of the maximum available cutting power. The power selection level as well as other functions, such as coagulation mode duration, may also be selected by pushing buttons 5 in response to a menu appearing on the display 4. The handpiece 2 is connected to the harmonic generator 1 by a coaxial cable 8. As illustrated in more detail in FIG. 1a and the '387 patent, the ultrasonic handpiece 2 houses an ultrasonic system for converting electrical energy to mechanical energy that results in longitudinal vibrational motion. The ultrasonic system comprises a transducer 9, a mounting device 10 and a surgical device 11 such as the scalpel blade and holder. The transducer 9 includes a stack of ceramic piezoelectric elements 12 with a motionless node at the center of the stack sandwiched between two aluminum cylinders 13 and 14. The transducer 9 is fixed to the mounting device 10 in a permanent manner. In turn, the mounting device 10 is attached to the housing at another motionless node by an integral ring 15. The mounting device 10, transducer 9 and the surgical device 11 are designed and fabricated to oscillate at the same resonant frequency, with each element tuned accordingly such that the resulting length of each such element is one-half wavelength. Expansion of the piezoelectric ceramic elements 12 results in the initiation of motion in the acoustic system of the transducer 9.

Detachably connected to the harmonic generator 1 is a foot switch 6 for causing activation of the device in a coagulation operation mode. A switch 6a is incorporated in the handpiece 2. However, the switch 6a as found in the art includes shortcomings such as a high risk of inadvertent activation and deactivation. In addition, long-term operation results in fatigue in the finger of the human operator of the handpiece 2.

Therefore, there is a general need in the art for an improved switch for use with an ultrasonic surgical handpiece. In particular, a need exists for a switch in an ultrasonic surgical handpiece that is easy-to-operate, reduces the risk of inadvertent activation/deactivation, and reduces fatigue in the finger of the human operator.

SUMMARY OF THE INVENTION

According to the invention, a finger-operated switch for activating and operating an ultrasonic surgical handpiece is provided. The power output of the surgical handpiece is responsive and proportional (linearly, nonlinearly proportional or in terms of a step function) to the pressure applied to the finger-operated switch. The finger-operated switch may include, but is not limited to: (1) electro-mechanical switches; (2) force sensitive resistors whose resistance is proportional to the force applied by the finger of the human operator of the surgical handpiece; (3) force sensitive capacitors whose capacitance is proportional to the pressure, deflection or compression of the insulation layer between two electrodes or is proportional to the spacing between the two conductive layers; (4) strain gauges mounted underneath or integral to the housing of the surgical handpiece such that the pressure applied thereto results in an output change in the strain gauges; (5) magnets or ferromagnets encased or embedded in an elastomer with a sensor inside the surgical handpiece that detects the field strength of the magnet and monitors changes relative to the force applied to the handpiece housing; and (6) piezo film or piezo ceramic material whose charge or voltage is proportional to the force applied.

BRIEF DESCRIPTION OF THE DRAWINGS

These and other features, aspects, and advantages of the invention will become more readily apparent with reference to the following detailed description of a presently preferred, but nonetheless illustrative, embodiment when read in conjunction with the accompanying drawings. The drawings referred to herein will be understood as not being drawn to scale, except if specifically noted, the emphasis instead being placed upon illustrating the principles of the invention. In the accompanying drawings:

FIG. 1 is a diagram illustrating an ultrasonic surgical system in accordance with the prior art;

FIG. 1a is a diagram illustrating the interior of the ultrasonic surgical handpiece of the surgical system shown in FIG. 1;

FIG. 2b is longitudinal cross-sectional view of an exemplary button switch according to the invention;

FIGS. 8, 8A, 9, 9a, 10, 10a, 10b, 11 and 12 are diagrams illustrating various embodiments for the ring switch with activation zones for the ultrasonic surgical handpiece according to the invention.

DETAILED DESCRIPTION OF THE PREFERRED EMBODIMENTS

Figure 2:
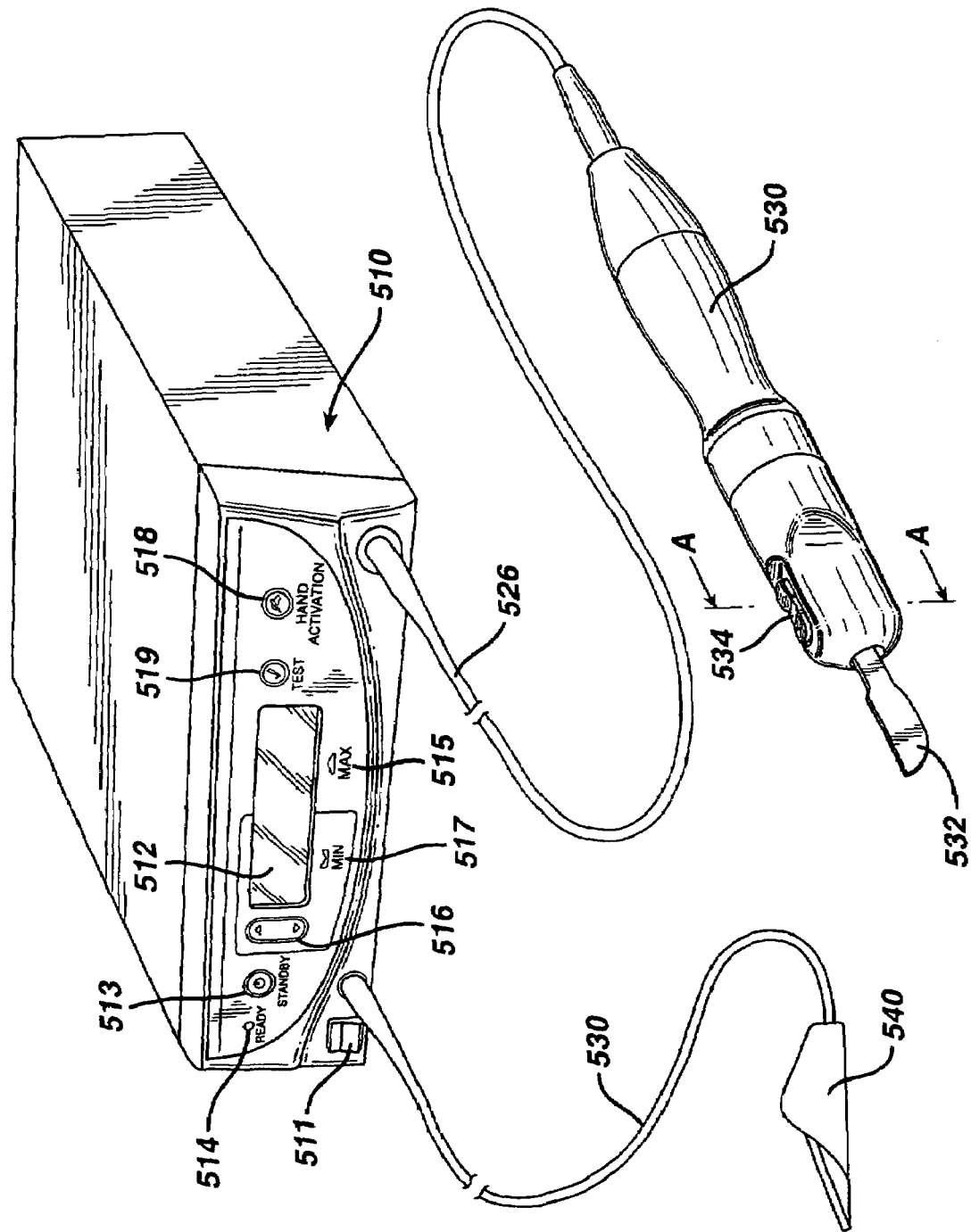
FIG. 2 is an illustration of a generator console for an ultrasonic surgical cutting and hemostasis system according to the invention.

FIG. 2 is an illustration of a system for implementing surgical procedures according to the invention. By means of a first set of wires in cable 526, electrical energy, i.e., drive current, is sent from the generator console 510 to a handpiece 530 where it imparts ultrasonic longitudinal movement to a surgical device or end effect or, such as a sharp scalpel blade 532. This blade can be used for simultaneous dissection and cauterization of tissue. The supply of ultrasonic current to the handpiece 530 may be under the control of a distally located switch 534 located on the handpiece, which is connected to the generator in console 510 via wires in cable 526. The generator may also be controlled by a foot switch 540, which is connected to the console 510 by another cable 550. Thus, in use a surgeon may apply an ultrasonic electrical signal to the hand piece, causing the blade to vibrate longitudinally at an ultrasonic frequency, by operating the switch 534 on the handpiece with his finger, or by operating the foot switch 540 with his foot.

The generator console 510 includes a liquid crystal display device 512, which can be used for indicating the selected cutting power level in various means, such as percentage of maximum cutting power or numerical power levels associated with cutting power. The liquid crystal display device 512 can also be utilized to display other parameters of the system. Power switch 511 is used to turn on the unit. While it is warming up, the "standby" light 513 is illuminated. When it is ready for operation, the "ready" indicator 514 is illuminated and the standby light goes out. If the unit is to supply maximum power, the MAX button 515 is depressed. If a lesser power is desired, the MIN button 517 is activated. This automatically deactivates the MAX button. The level of power when MIN is active is set by button 516.

When power is applied to the ultrasonic hand piece by operation of either switch 534 or 540, the assembly will cause the end effector (surgical scalpel or blade) to vibrate longitudinally at approximately 55.5 kHz (or about 25 kHz in another embodiment), and the amount of longitudinal movement will vary proportionately with the amount of driving power (current) applied, as adjustably selected by the user. When a relatively high level of cutting power is applied, the blade is designed to move longitudinally in the range of about 40 to 100 microns at the ultrasonic vibrational rate. Such ultrasonic vibration of the blade will generate heat as the blade contacts tissue, i.e., the acceleration of the blade through the tissue converts the mechanical energy of the moving blade to thermal energy in a very narrow and localized area. This localized heat creates a narrow zone of coagulation, which will reduce or eliminate bleeding in small vessels, such as those less than one millimeter in diameter. The cutting efficiency of the blade, as well as the degree of hemostasis, will vary with the level of driving power applied, the cutting rate of the surgeon, the nature of the tissue type and the vascularity of the tissue.

Figure 2A:
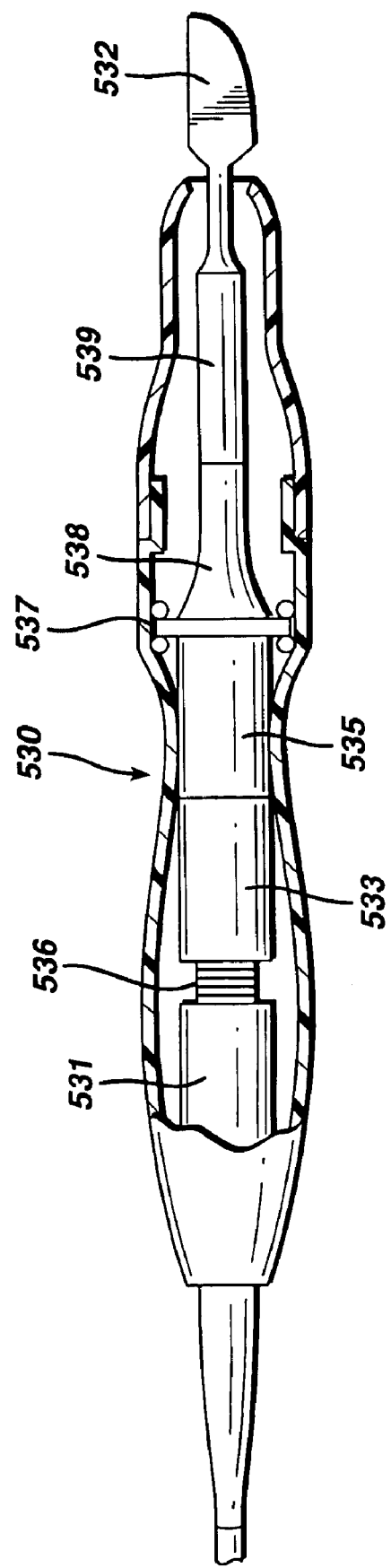
FIG. 2a is a schematic view of a cross section through the ultrasonic scalpel handpiece of the system of FIG. 2.

As illustrated in more detail in FIG. 2a, the ultrasonic handpiece 530 houses a piezoelectric transducer 536 for converting electrical energy to mechanical energy that results in longitudinal vibrational motion of the ends of the transducer. The transducer 536 is in the form of a stack of ceramic piezoelectric elements with a motion null point located at some point along the stack. The transducer stack is mounted between two cylinders 531 and 533. In addition a cylinder 535 is attached to cylinder 533, which in turn is mounted to the housing at another motion null point 537. A horn 538 is also attached to the null point on one side and to a coupler 539 on the other side. Blade 532 is fixed to the coupler 539. As a result, the blade 532 will vibrate in the longitudinal direction at an ultrasonic frequency rate with the transducer 536. The ends of the transducer achieve maximum motion with a portion of the stack constituting a motionless node, when the transducer is driven with maximum current at the transducers' resonant frequency. However, the current providing the maximum motion will vary with each hand piece and is a value stored in the non-volatile memory of the hand piece so the system can use it.

The parts of the handpiece are designed such that the combination will oscillate at the same resonant frequency. In particular, the elements are tuned such that the resulting length of each such element is one-half wavelength. Longitudinal back and forth motion is amplified as the diameter closer to the blade 532 of the acoustical mounting horn 538 decreases. Thus, the horn 538 as well as the blade/coupler are shaped and dimensioned so as to amplify blade motion and provide harmonic vibration in resonance with the rest of the acoustic system, which produces the maximum back and forth motion of the end of the acoustical mounting horn 538 close to the blade 532. A motion from 20 to 25 microns at the transducer stack is amplified by the horn 538 into blade movement of about 40 to 100 microns.

FIG. 2b is a more detailed longitudinal cross-sectional view of an exemplary button switch according to the invention. This design, as well as others disclosed herein, allows for operation of the hand pieces in various modes, and is also described in related U.S. patent application Ser. No. 09/693,549, commonly assigned to the same assignee as the present application, having the title RING CONTACT FOR ROTATABLE CONNECTION OF SWITCH ASSEMBLY FOR USE IN AN ULTRASONIC SURGICAL SYSTEM and filed on Oct. 20, 2000, which is incorporated herein by reference. The switch for use with an ultrasonic surgical handpiece according to the invention includes two independent switches under generally the same elastomer or flexible thin metallic skin with a middle recess for resting a finger of a human operator. The middle recess serves as a tactile reference point, as the blade and handpiece are non-symmetrically configured, for the human operator which avoids inadvertent activation or deactivation. In addition, the middle recess provides a safe, convenient spot for the human operator to grasp the handpiece and the switch without inadvertently activating the switch. The switch is also ergonomically designed and tested to be comfortably grasped by small or big hands of any human that may operate the handpiece.

Referring to FIG. 2b, the ultrasonic surgical handpiece according to the invention provides a switch that includes a pair of switch button members 270, detachably secured within the button sections 214, which are about 180° apart to permit convenient grasping of the handpiece yet avoid inadvertent activation or deactivation. Each switch button member 270 has an upper surface 272 and an opposing lower surface 274 with the lower surface 274 seating against the outer shell 201. First and second posts 276, 278, respectively, extend outwardly away from the lower surface 274 of the switch button member 270. The first and second posts 276, 278 are spaced apart from one another with a center traverse wall being formed therebetween. The upper surface 272 includes a first raised section 282 and a second raised section 284 spaced therefrom with a center recessed section 286 being formed therebetween. The upper surface 272 is thus slightly beveled as the switch button member 270 transitions from the center recessed section 286 to the first and second raised sections 282, 284. In the illustrated embodiment, the first post 276 is disposed generally below the first raised section 282 and the second post 278 is disposed generally below the second raised section 284 so that when a user presses downwardly upon the first raised section 282, the first post 276 is also directed downward. Similarly, when the switch is pressed downwardly upon the second raised section 284, the second post 278 is directed downward. In another embodiment according to the invention, the switch is a dome switch which includes a dome of a thin metallic skin that collapses downward as pressure is applied thereto.

The switch button members 270 are designed to act as a depressable switch button for selectively causing activation of the ultrasonic surgical handpiece according to the invention. The switch button members 270 are formed of suitable materials, such as plastic materials, and preferably the switch button members 270 are formed of a resilient plastic material. In one exemplary embodiment, the switch button members 270 are formed of silicon which permits the members to be sufficiently resilient enough so that they may be fitted and secured within the button sections 214 to seal internally and also provide an engagement surface for a finger or thumb of a human operator during operation of the handpiece. In one aspect of the present invention, the contour of the switch button member 270 permits a fingertip of a human operator to easily rest between the first and second raised sections 282 and 284. In other words, the finger tip or thumb of a human operator seats and rests within the center recessed section 286 without actuating the switch mechanism. The switch button members 270 are disposed within the button sections 214. The switch button members 270 are spaced about 180° from one another. A pair of fasteners 300 are positioned beneath the center traverse wall. Each button section 214 formed in the outer shell 201 contains openings formed therein and spaced apart from one another for receiving the first and second posts 276 and 278 of the switch button member 270. The exemplary switch mechanism is an electro-mechanical switch that is depressable for activation and, according to the present invention, two switch button members 270 form, at least in part, the switch. Each switch button member 270 has two switch sites. For example, the first raised section 282 and the first post 276 are associated with a first switch site and the second raised section 284 and the second post 278 are associated with a second switch site. Preferably, the first switch site of one switch button member 270 is generally the same as the first switch setting of the other switch button member 270 disposed about 180° therefrom. In one exemplary embodiment, the first switch site is a maximum power setting (MAX) and the second switch setting is an intermediate power setting which can include a minimum (MIN). It will be understood that the opposite may equally be true, in that the first switch setting may be designed for causing the transmission of intermediate power to the handpiece according to the invention and the second switch setting will then cause the transmission of maximum power to the handpiece.

Distally placing the switch on the handpiece according to the invention provides significant advantages over the prior art. As switches in the art are placed on the non-distal end (e.g., medial or proximal end) of the handpiece, blade control becomes ineffective since operating the blade with a switch proximally positioned on the handpiece creates substantially uncontrollable jitter when using the blade for cutting or coagulation on a tissue. Pressing the switches proximally located on the handpiece has negative effects and disrupts blade positioning on the tissue. This is particularly inconvenient for performing surgery and burdensome for a human operator in controlling the handpiece. Positioning the switches on the distal end of the handpiece significantly reduces the occurrence of blade jitter and generally improves operational control of the handpiece by the human operator.

The switch according to the invention is configured on the distal end of the handpiece, to permit accurate blade control, handpiece handling and to conveniently operate the switches without jitter of the blade, with the scalpel blade 532 which is screwed onto the handpiece and rotatable. The switch according to the invention, in relation with the blade 532, is configured so that the switch is generally aligned by a human operator with the blade as it is rotated or indexed to a particular blade symmetry. The alignment by the human operator (or user alignment) can be incremental (using indents or detents), continuous or indexed to particular symmetries. The switch can also be generally aligned with the rotating blade with a particular symmetry, depending on the configuration of the handpiece and needs of the human operator for cutting or coagulation. Other embodiments of the switch according to the invention include a switch with a single button member, metal dome switches whose dome collapses for contacting a circuitry on a printed circuit board (PCB), which is described in related U.S. patent application Ser. No. 09/693,549, commonly assigned to the same assignee as the present application, having the title RING CONTACT FOR ROTATABLE CONNECTION OF SWITCH ASSEMBLY FOR USE IN AN ULTRASONIC SURGICAL SYSTEM and filed on Oct. 20, 2000.

The switch according to the invention can also be used for controlling functions in the generator console 510 including initiating diagnostic functions on the handpiece, and implementing a standby mode. In a particular embodiment according to the invention, the standby mode of operating the handpiece, which renders the switch inoperable, is activated by applying pressure to both buttons of the switch at generally the same time. The standby mode is subsequently deactivated by doing the same, i.e., by applying pressure to both buttons of the switch at generally the same time.

Figure 3A:
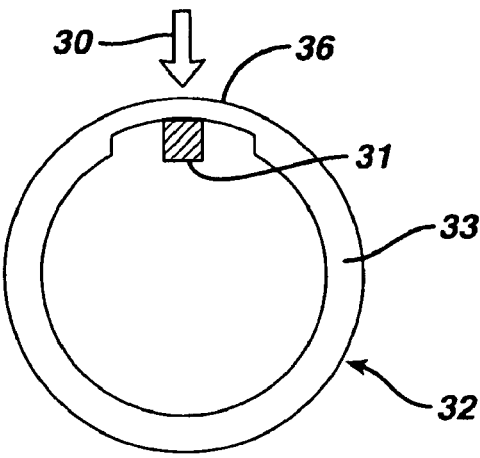
FIG. 3a is a diagram illustrating a housing deflection embodiment of the switch for controlling the ultrasonic surgical handpiece according to the invention.

FIG. 3a is a cross-sectional view (taken at A-A of FIG. 2) that illustrates a housing deflection embodiment of the switch for an ultrasonic surgical handpiece according to the invention. This one-push button design, as well as others disclosed herein, allows for operation of the hand pieces in various modes. The switch according to the housing deflection embodiment as shown in FIG. 3a includes a pressure sensor 31 mounted inside the housing 33 of the ultrasonic handpiece 32 where it is relatively protected from the environment. The sensor 31, located on the internal side of a thin wall area 36 of the handpiece housing 33, detects pressure 30 applied by a finger of a human operator of the handpiece 32. The sensor 31 can be, but is not limited to, an electro-mechanical switch, a strain gauge, a pressure sensitive resistor/sensor combination, a hall effect device/magnet combination, reed switch/magnet combination, a piezo element, or a capacitance sensor which detects the force applied to the thin wall area 36. As finger pressure 30 is applied to the thin wall 36, the portion of the handpiece housing 33 at the thin wall 36 deflects, which is detected by the sensor 31 that outputs a response signal to the handpiece. This signal is conveyed through cable 526 to a detection circuit in the generator console 510 that controls the application of power to the transducers in the handpiece in response thereto.

The switch according to the invention provides multi-level activation and operation via the thin wall area 36, where various levels of applied pressure determine the mode of operation for the handpiece 32. In accordance with the magnitude of the finger pressure 30, the output from the sensor 31 causes the handpiece 32 to be "on" or "off" or more particularly, operating with a power level proportional to the finger pressure 30 as applied to the thin wall 36. For example, after initial activation of the handpiece 32 ("on"), a very low applied pressure 30 enables low power level operation of the handpiece 32. A somewhat higher applied pressure 30 enables higher power level operation of the handpiece 32, without excessive finger pressure fatigue for the human operator of the handpiece 32.

Figure 3B:
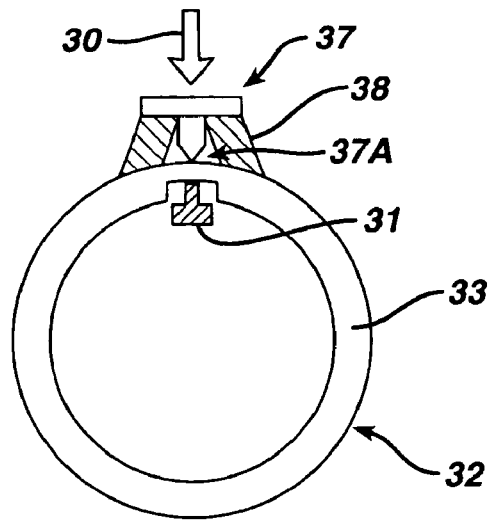
FIG. 3b is a diagram illustrating a pressure button embodiment of the switch for controlling the ultrasonic surgical handpiece according to the invention.

FIG. 3b is a cross-sectional view (taken at A-A of FIG. 2) that illustrates a pressure button embodiment of the switch for an ultrasonic surgical handpiece according to the invention. According to the pressure button embodiment which is a one-push button design, the handpiece 32 includes a button 37 mounted on a button support 38 on the exterior of the handpiece housing 33. A pressure sensor 34 is located inside the handpiece housing 33 and is separated from the button 37 by a thin wall area 36 of the handpiece housing 33. When finger pressure 30 is applied to the button 37, the thin wall area 36 is deflected and a concentrated, focused pressure is detected by the pressure sensor 34. The thumbnail-like design of the button having a pointy end 37A towards the pressure sensor 34 ensures transmission of concentrated pressure to the pressure sensor 34, which requires less effort by a human operator during application of pressure to the button 37. The pressure sensor 34 detects the force applied to the thin wall area 36 and outputs a response signal to the handpiece 32 which transmits it to a detection circuit in the generator console 510. The switch according to the invention provides multi-level activation and operation via the thin wall area 36, where various levels of applied pressure determine the mode of operation for the handpiece 32. In accordance with the magnitude of the finger pressure 30, the output from the sensor 31 causes the handpiece 32 to be "on" or "off" or more particularly, operating with a power level proportional to the finger pressure 30 as applied.

Figure 3C:
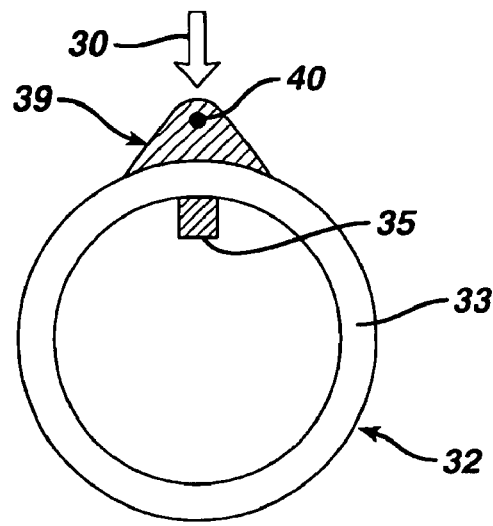
FIGS. 3c, 3d, 3e and 3f are diagrams illustrating various magnet button embodiments of the switch for controlling the ultrasonic surgical handpiece according to the invention.

FIG. 3c is a cross-sectional view (taken at A-A of FIG. 2) that illustrates a magnet button embodiment of the switch for an ultrasonic surgical handpiece 32 according to the invention. According to this embodiment which is a one-push button design, the handpiece 32 includes an elastomeric pad 39 with a magnet 40 (or, ferromagnetic element, metallic element, or coil) embedded therein. A sensor 35 is located inside the handpiece housing 33 and detects the field strength of the magnet. Sensor 35 monitors changes in field strength related to the force applied to the handpiece housing 33. The sensor 35 can be, but is not limited to, a reed switch; a hall effect device; or an inductance, proximity, or capacitance sensor, which responds to the relative position of a neighboring piece of magnet or ferromagnet or material (e.g., magnet 40). As finger pressure 30 is applied to the elastomeric pad 39, the magnet 40 moves closer to the sensor 35. The switch according to the invention provides multi-level activation and operation, where various levels of applied pressure determine the mode of operation for the handpiece 32. Depending on the magnitude of the finger pressure 30, the output from the sensor 35 causes the handpiece 32 to be "on" or "off" or more particularly to operate with a power level proportional to the finger pressure 30 applied.

Figure 3D:
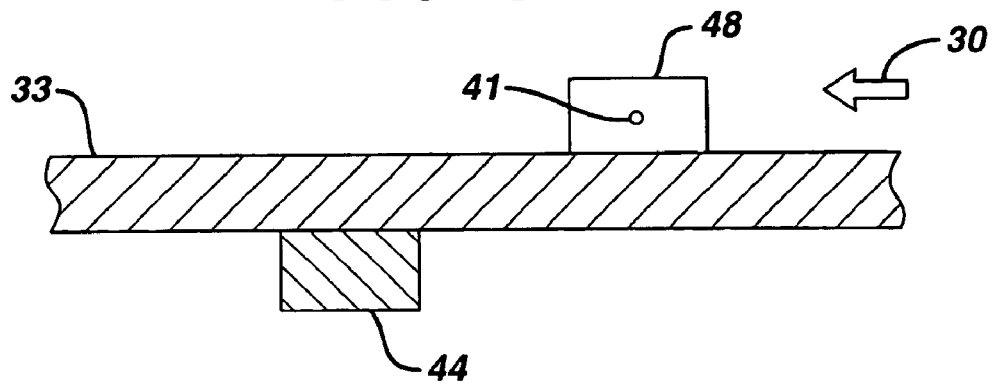

FIG. 3d is a partial cross-sectional view (taken at A-A of FIG. 2) that illustrates another magnet button embodiment of the switch for an ultrasonic surgical handpiece 32 according to the invention. FIG. 3d is similar to FIG. 3c, except that it is greatly enlarged and the magnet 41 is embedded in a slide button 48 as opposed to the elastomeric pad 39 of FIG. 3c. According to this particular embodiment, the handpiece 32 includes a slide button 48 slidably attached on the outside of the handpiece housing 33 with a magnet 41 (or, ferromagnetic element, metallic element, or coil) embedded therein. A sensor 44 is located inside the handpiece housing 33 and detects the field strength of the magnet. In particular, sensor 44 monitors changes in the magnet's field strength related to the force applied to the handpiece housing slide button. The sensor 44 can be, but is not limited to, a reed switch; a hall effect device; or an inductance, proximity, or capacitance sensor, which responds to the relative position of a neighboring piece of magnet or ferromagnet (e.g., magnet 41). As finger pressure 30 is applied to the slide button 48, the embedded magnet 41 moves closer to the sensor 44. If desired, slide button 48 can be attached to a spring which tends to restore it to its initial position. As a result, the position of slide button 48 is proportional to the amount of force applied, and not just simply the application of some force, for a period of time.

The switch according to the embodiment of FIG. 3d provides multi-level activation and operation, where various levels of applied pressure on the application of pressure for various periods determine the mode of operation for the handpiece 32. Depending on the magnitude of the finger pressure 30 or where the switch is when the pressure is released (assuming no spring return), the output from the sensor 44 causes the handpiece 32 to be "on" or "off" or more particularly, operating with a power level proportional to the position or finger pressure 30 as applied.

Figure 3E:
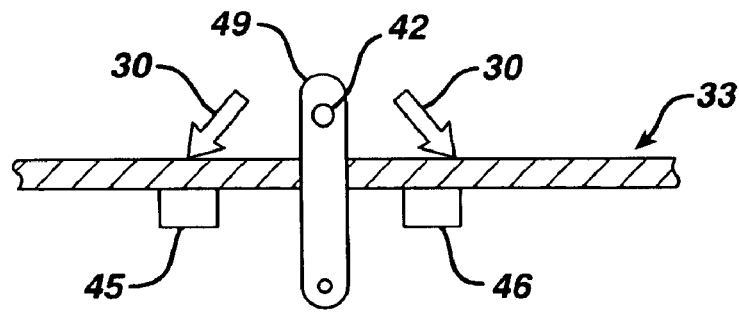

FIG. 3e is a partial cross sectional view (taken at A-A of FIG. 2) that illustrates another magnet button embodiment of the switch for an ultrasonic surgical handpiece 32 according to the invention. FIG. 3e is similar to FIG. 3d, except that the magnet 42 is embedded in a lever 49 as opposed to the slide button 48 of FIG. 3d. According to this particular embodiment, the handpiece 32 has the lever 49 extending from the outside to the inside of the handpiece housing 33, with a magnet 42 (or, ferromagnetic element, metallic element, or coil) embedded therein. The lever 49 is made of an elastic material and responds to finger pressure 30 so as to be bendable to the left or right. Two sensors 45 and 46 are located inside the handpiece housing 33 that detect the field strength of the magnet and monitor changes therein relative to the force applied to the lever 49. The sensors 45 and 46 can be, but are not limited to a reed switch; a hall effect device; or an inductance, proximity, or capacitance sensor which responds to the relative position of a neighboring piece of magnet or ferromagnet (e.g., magnet 42) as plastic lever 49 is bent. As finger pressure 30 is applied to the lever 49, the embedded magnet 42 moves closer to either sensor 45 or sensor 46. The switch according to the invention thus provides multi-level activation and operation, where various levels of applied pressure and the direction of that pressure on lever 49 determine the mode of operation for the handpiece 32. Depending on the magnitude and direction of the finger pressure 30, the output from the sensor 45 causes the handpiece 32 to be "on" (if the lever 49 is pressed toward the sensor 45 and against the handpiece housing 33 fully), or operating with a power level proportional to the finger pressure 30 as applied. Similarly, depending on the magnitude of the finger pressure 30, the output from the sensor 46 causes the handpiece 32 to be "off" (if the lever 49 is pressed toward the sensor 46 and against the handpiece housing 33 fully), or operating with a power level proportional to the finger pressure 30 as applied.

As an alternative, if no pressure is applied and sensors 45, 46 receive relatively equal field strengths, the handpiece can be off. It can then operate in one mode (e.g. cutting) at different levels, as the lever is pressed toward sensor 45 and in a different mode (e.g. coagulation) at different levels as the lever is pressed towards sensor 46.

Figure 3F:
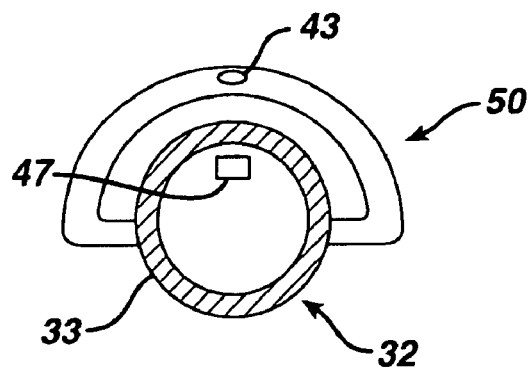

FIG. 3f is a cross sectional view (taken at A-A of FIG. 2) that illustrates another magnet button embodiment of the switch for an ultrasonic surgical handpiece 32 according to the invention. FIG. 3f is similar to FIG. 3c, except that the magnet 43 is embedded in an elastic ring 50 as opposed to the elastomeric pad 39 of FIG. 3c. A sensor 47 is located inside the handpiece housing 33 that detects the field strength of the magnet 43 and monitors changes in the field strength relative to the force applied to the ring 50 toward the housing 33. The sensor 47 can be, but is not limited to a reed switch; a hall effect device; or an inductance, proximity, or capacitance sensor which responds to the relative position of a neighboring piece of magnet or ferromagnet (e.g., magnet 43). As finger pressure is applied to the ring 50, the embedded magnet 43 moves closer to the sensor 47. The switch according to the invention provides multi-level activation and operation, where various levels of applied pressure on the elastic ring 50 determine the mode of operation for the handpiece 32. Depending on the magnitude of the finger pressure, the output from the sensor 47 causes the handpiece 32 to be "on" or "off" or more particularly, operating with a power level proportional to the finger pressure as applied.

Figure 4A:
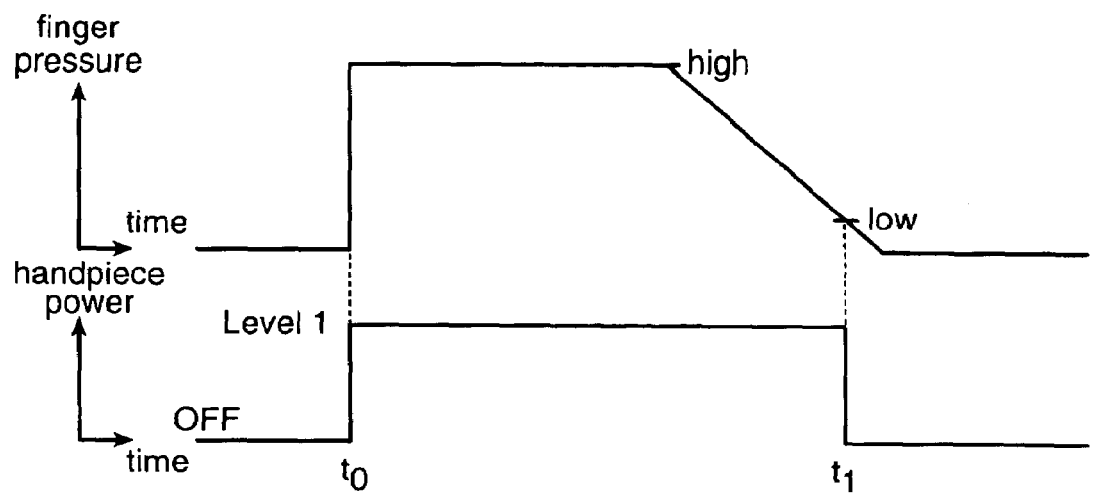
FIGS. 4a and 4b are diagrams illustrating the various power levels of operation for the-ultrasonic surgical handpiece controlled by the switch according to the invention.

The switch according to the invention, as described herein and shown in the accompanying figures, provides multi-level activation and operation at different power levels, where various levels of applied pressure determine the mode of operation for the ultrasonic surgical handpiece. FIG. 4A is a diagram that illustrates the operation of a single power level embodiment of the ultrasonic surgical handpiece having a switch according to the invention. The relationship of finger pressure applied to the switch and the power level of the ultrasonic surgical handpiece referenced by time is shown. A high finger pressure is required to activate the handpiece at time t0. Once activated, the handpiece operates at power level 1. Thereafter, only a sufficiently high finger pressure (higher than the "low" finger pressure as marked) is needed to keep the handpiece operative at power level 1. Once the finger pressure applied to the switch equals or falls below the "low" threshold at time t1, the handpiece turns "off" and ceases to receive output power.

Figure 4B:
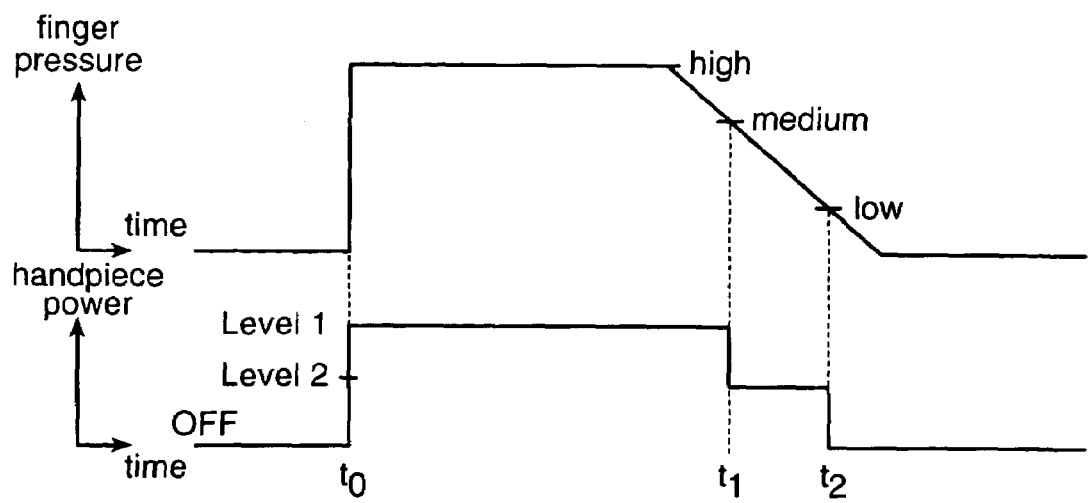

FIG. 4b is a diagram that illustrates the operation of a dual power level embodiment of the ultrasonic surgical handpiece having a switch according to the invention. The relationship of finger pressure applied to the switch and the power level of the ultrasonic surgical handpiece referenced by time is shown. A high finger pressure is required to activate the handpiece at time t0. Once activated, the handpiece operates at power level 1. Once the finger pressure applied to the switch equals or falls below the "medium" threshold at time t1, the handpiece operates at power level 2. Thereafter, if the finger pressure equals to or falls below the "low" threshold at time t2, the handpiece turns "off" and ceases to receive output power.

FIGS. 4a and 4b merely illustrate two embodiments, i.e., the single power level and the dual power level embodiments, respectively, of the multi-level power operation for the ultrasonic surgical handpiece having a pressure sensitive switch according to the invention. Other multi-level embodiments, e.g., three-level, four-level, etc., are also considered to be within the scope and spirit of the present invention.

Accordingly, the invention provides a method for controlling an ultrasonic surgical handpiece using a switch located on the housing of the handpiece, which comprises the steps of: (1) monitoring the pressure applied to the housing a lever or ring compressors; (2) activating the surgical handpiece at a high power level if the monitored pressure reaches a high threshold; (3) operating the surgical handpiece at a corresponding intermediate power level if the monitored pressure reaches a specific intermediate threshold below the high threshold; and (4) deactivating the surgical handpiece if the monitored pressure is below a low threshold which is less than the specific intermediate threshold. The finger-operated switch includes, but is not limited to, (a) an electro-mechanical switch, (b) force sensitive resistors whose resistance is proportional to the force applied by the finger of the human operator of the surgical handpiece; (c) force sensitive capacitors whose capacitance is proportional to the pressure, deflection or compression of the insulation layer between two electrodes or is proportional to the spacing between the two conductive layers; (d) strain gauges mounted underneath or integral with the housing of the surgical handpiece such that the pressure applied thereto results in an output change in the strain gauges; (e) magnets or ferromagnets encased or embedded in an elastomer with a sensor inside the surgical handpiece that detects the field strength of the magnet and monitors changes relative to the force applied to the handpiece housing; and (f) piezo film or piezo ceramic materials whose charge or voltage is proportional to the force applied.

Figure 5:
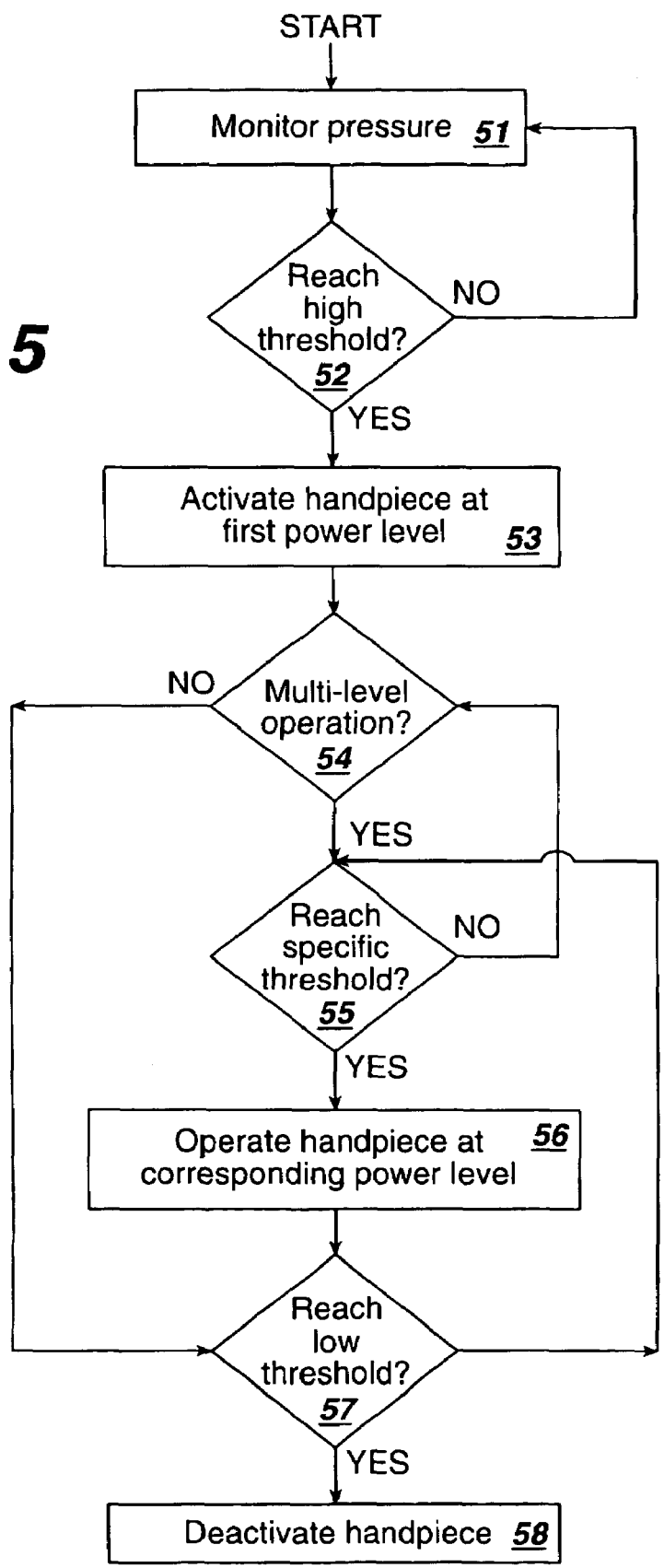
FIG. 5 is a flow diagram generally illustrating the method according to the invention for controlling the ultrasonic surgical handpiece using a switch.

FIG. 5 is a flow diagram that illustrates the method according to the invention for controlling the ultrasonic surgical handpiece using a pressure-sensitive switch. In step 51, the pressure applied to the housing of the surgical handpiece, elastomer material mounted on the housing, an elastic lever, or an elastic ring is monitored. The monitored pressure is tested against a high threshold (step 52). If the monitored pressured does not reach the high threshold, the control flow reverts to step 51 which continues the monitoring of the pressure applied to the housing of the surgical handpiece. If the monitored pressure reaches the high threshold, the surgical handpiece is activated to operate at a first power level (step 53). If the surgical handpiece does not have multi-level operational capability (step 54), then control flow goes to step 57 and the monitored pressure is tested against a low threshold. If the monitored pressure reaches the low threshold, then the surgical handpiece is deactivated (step 58). This operation could also be based on a single threshold. In particular, if it is determined that the pressure has exceeded a minimum level, the power is fully turned on and remains there until it is determined that the pressure has fallen below the single minimum threshold.

If the surgical handpiece can operate at multiple power levels (step 54), then in the method of FIG. 4, the monitored pressure is tested against a plurality of specific thresholds (step 55). If the monitored pressure reaches a specific intermediate threshold, then the surgical handpiece operates at a power level corresponding to that specific threshold (step 56). In step 57, if the monitored pressure reaches the low threshold, then the surgical handpiece is deactivated. If the monitored pressure has not yet reached the low threshold, the control flow reverts back to step 55 and the surgical handpiece continues to operate at multiple power levels.

When the system has multiple thresholds, it can step down from a minimum various power levels as the pressure is released. Alternatively it can turn on at a minimum level and step up to higher levels of power as the pressure is increased.

In a further embodiment, the switch according to the invention includes a sensor that is flat and tape-like. This type of sensor is made of piezo-electric material or a pressure-sensitive resistor (or resistor tape). Such a flat tape-like sensor provides a very low profile sensing means that is relatively easily mounted on or in a surgical handpiece. With the flat tape-like sensor, the switch is configured as an "active zone" on or around the surgical handpiece for activating and controlling the handpiece. The switch is activated when the surgeon's finger is on or applies pressure to the active zone.

Figure 6:
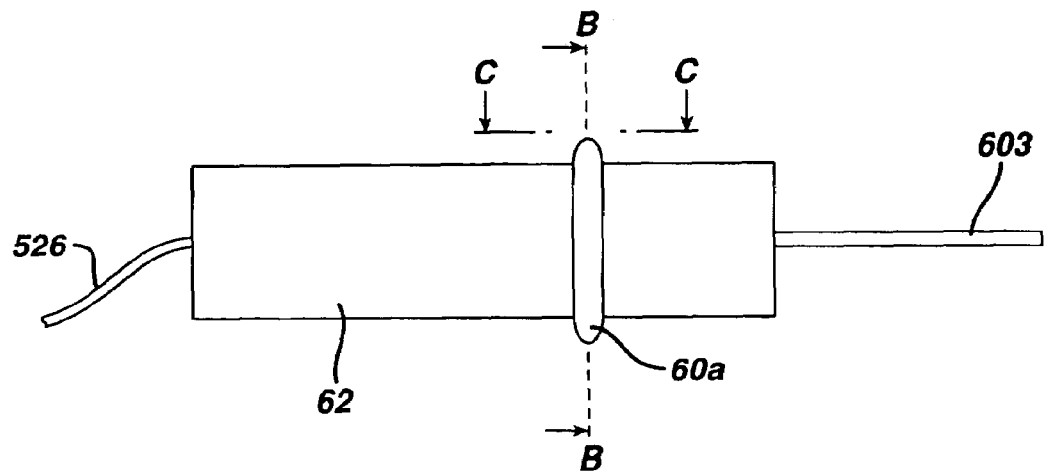
FIGS. 6, 6b and 6c are diagrams illustrating a ring embodiment (and cross-sectional views thereof) for the switch for the surgical handpiece according to the invention.

FIG. 6 is a diagram that illustrates a ring embodiment for the switch for the handpiece according to the invention. A harmonic generator 510, illustrated in FIG. 2, provides electrical energy to the handpiece 62 which imparts ultrasonic longitudinal movement to a surgical device, such as a sharp scalpel blade 603 used for dissection or coagulation. The handpiece 62 is connected to the harmonic generator 510 by the coaxial cable 26X. The ring switch 60a is a ring-like circumferential appendage on the handpiece 62, located near the distal end thereof. The handpiece 62 is activated when pressured is applied, e.g, by a finger of a human operator of the handpiece 62, to the side wall of the switch 60a. The mode of activation (e.g., cutting or coagulation) is determined by which side of the ring switch 60a is pressed upon. Pressure may be applied in a direction that is not perpendicular to the handpiece 62 and still activate it. Pressure applied to the top of the ring switch 60a which is perpendicular to the handpiece 62, depending on the particular embodiment, can lead to a number of functions. That is, the pressure applied to the top of the ring switch 60a may be ignored on the one hand, invoke a third mode of operation other than cutting and coagulation, or default to one of the two selectable modes of operation. For example, when the ring switch 60a is pressed, the base of the ring switch 60a applies pressure to one of several pressure-sensitive sensors which can activate the handpiece 62. One sensor 65 is activated when the ring switch 60a is pushed from one direction, another sensor 67 is activated when the ring is pushed from the other direction, and both sensors are activated when the ring is pushed upon from the above with a pressure force perpendicular to the handpiece 62.

The ring switch 60a can be mounted directly or indirectly to a single sensor 69 such that when one side of the ring is pressed, the sensor is pushed upon. Conversely, when the opposing side of the ring is pushed, the sensor is pulled upon, or any pre-biased pressure is thereby reduced. Electronic circuitry in the sensor or handpiece can detect whether push or pull (or reduced pressure) is present and evoke a corresponding mode of operation in response.

In the alternative, the ring itself can be the sensor, where the ring switch 60a is made of a piezo material that, when pressed thereupon, generates a voltage proportional to the force applied and the direction of that applied force. Pressing against one side of the ring generates one polarity signal and pressing against the other side generates an opposite polarity signal, thereby permitting at least two modes of operation from a single ring/sensor. Furthermore, the ring switch 60a can be non-piezo such as a force-sensitive resistor, yet mechanically coupled to a piezo ring which responds proportionally to pressure applied to the ring and whose output polarity is dependent on which side of the ring is pressed.

Figure 6B:
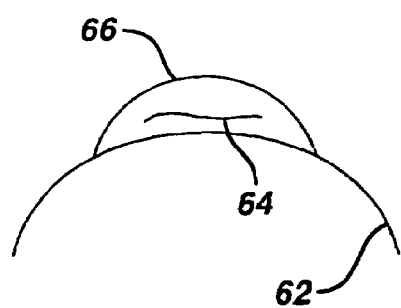
Figure 6C:
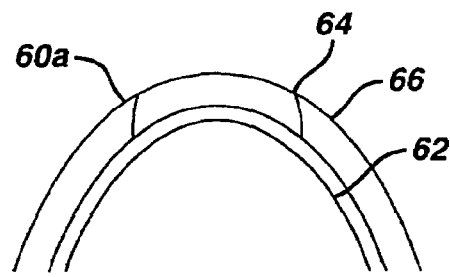

The ring switch 60a can also utilize a capacitance transducer, which comprises a relatively inflexible metal center ring 64 with an outer layer of foam or elastomer and a flexible metal ring electrode 66 (FIG. 6a, which is a cross section along line B-B in FIG. 6; and FIG. 6b a cross section along line C-C in FIG. 6). When pressure is applied to one side of the ring, the pressure applied against the outer ring causes it to be deflected and thereby depress the foam or elastomer, which brings the outer ring closer to the center ring and thereby reduces the capacitance in proportion to the pressure applied.

In a further embodiment, the switch 60a can function as a switch due to the hysteresis effect. Hysteresis is the lagging of an effect behind its cause, as when the change in magnetism of a body lags behind changes in the magnetic field. The switching functionality is achieved per the lagging or retardation of the hysteresis effect when the pressure applied or forces acting upon the switch 60a are changed, and per the temporary resistance to change from a condition previously induced in magnetism or thermolelectricity (e.g., on reversal of polarity).

The ring switch 60a can also be one piece or segmented into two or more pieces. Segmenting the ring substantially improves the localization of sensor activation and reduces potential mechanical artifact activation of the sensor at ring locations distant to where the pressure is being applied. Segmentation also provides the ability to deactivate or reduce the sensitivity of selected segments for the convenience of the end user of the handpiece 62.

In addition, the ring switch 60a serves as a convenient reference point that provides visual tactile feedback of where to apply pressure for activating the handpiece 62. The ring switch 60a can also be used to indicate activation status. For example, the ring can be transparent or translucent, and becomes illuminated during activation or changes colors according to different modes of operation for the handpiece 62.

Figure 7A:
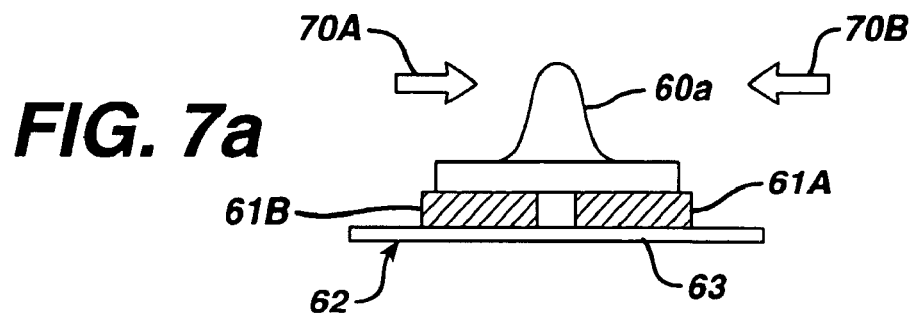
FIGS. 7a through 7i are diagrams showing partial cross sectional views of various embodiments of the ring switch for the ultrasonic surgical handpiece according to the invention.

FIG. 7a is a partial cross-sectional view of an embodiment of the ring switch 60a (taken at line C-C of FIG. 6) for the handpiece 62 according to the invention. According to this particular embodiment, the ring switch 60a, on the outside of the housing 63 of the handpiece 62, sits on top of two sensors 61A and 61B. As pressure 70A is applied to the ring 60a in one direction, sensor 61A detects that pressure and starts a mode of operation, e.g., activate the handpiece 62. As pressure 70B is applied to the ring 60a in the opposing direction, sensor 61B detects that pressure and starts a corresponding mode of operation, e.g., deactivate the handpiece 62, or proportionally reduces the power by which the handpiece 62 is operating, depending on the amount of pressure applied.

Figure 7B:
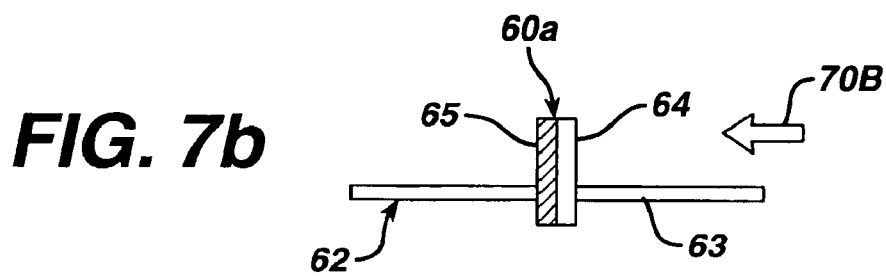

FIG. 7b is a partial cross-sectional view of another embodiment of the ring switch 60a (taken at line C-C of FIG. 6) for the handpiece 62 according to the invention. According to this particular embodiment, the ring switch 60a itself is the sensor which comprises a piezo portion 64 and a substrate 65 made of suitably deformable, flexible material. When pressure 70B is applied against the piezo portion 64, the ring switch 60a generates an output voltage proportional to the force applied (pressure 70B) and the direction of that applied force, and results in a polarity signal. The substrate 65 adds strength to the ring switch 60a. When pressure 70A is applied against the substrate 65 in the other direction, the ring switch 60a generates an opposing or different polarity signal than the polarity signal resulting from pressure 70B, thereby permitting at least two modes of operation (such as cutting or coagulation) from a single ring/sensor.

Figure 7C:
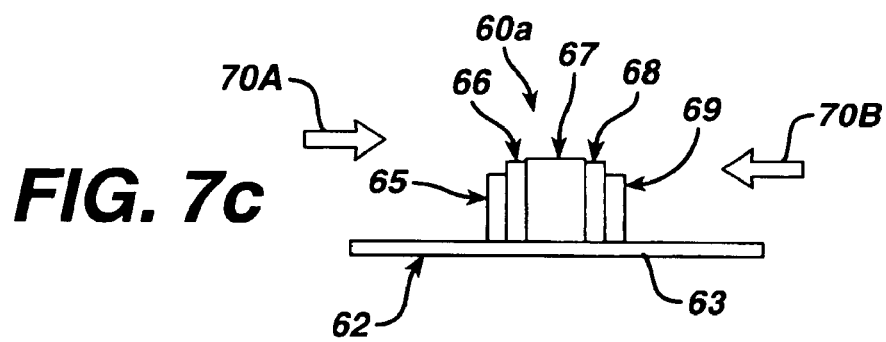

FIG. 7c is a partial cross-sectional view of another embodiment of the ring switch 60a (taken at C-C of FIG. 6) for the handpiece 62 according to the invention. According to this particular embodiment, the ring switch 60a includes a capacitance transducer comprising, a center ring 67, which is made of a conductive material such as a relatively inflexible metal, an outer layer of insulative ring 66 made of foam or elastomer, a conductive ring 65 which is an electrode made of a relatively flexible metal, another outer layer of insulative ring 68 also made of foam or elastomer on the other side of center ring 67, and another conductive ring 69 which is an electrode with an opposite polarity also made of a relatively flexible metal. When pressure 70A is applied to one side of the ring switch 60a, the insulative ring 66 is deflected and the foam or elastomer is depressed, which brings the conductive ring 65 closer to the center ring 67 and thereby reduces the capacitance in proportion to the pressure 70A as applied. The change in the capacitance between the conductive ring 65 and the center ring 67 activates the handpiece, causes the handpiece 62 to run in a specific mode of operation (such as cutting or coagulation), or proportionally increases the speed of operation depending on the amount of pressure 70A as applied. Conversely, when pressure 70B is applied to the other side of the ring switch 60a, the insulative ring 68 is deflected and the foam or elastomer is depressed, which brings the conductive ring 69 closer to the center ring 67 and thereby reduces the capacitance in proportion to the pressure 70B as applied. The change in the capacitance between the conductive ring 69 and the center ring 67 deactivates the handpiece, causes the handpiece 62 to run in a corresponding mode of operation (such as cutting or coagulation), or proportionally reduces the speed of operation depending on the amount of pressure 70B as applied.

Figure 7D:
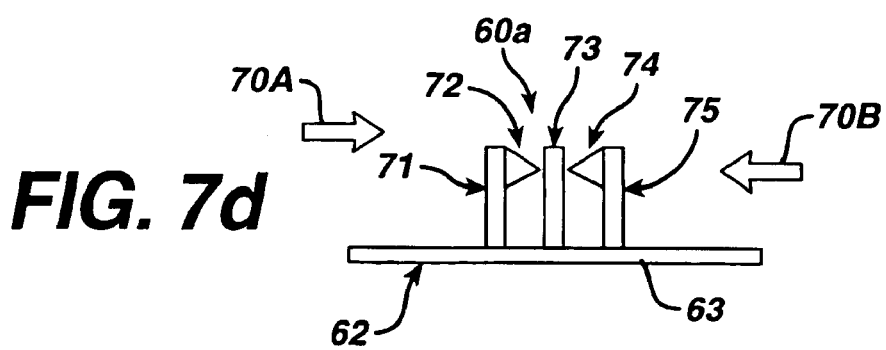

FIG. 7d is a partial cross-sectional view of a further embodiment of the ring switch 60a (taken at C-C of FIG. 6) for the handpiece 62 according to the invention. According to this particular embodiment, the ring switch 60a includes a center ring 73, which is made of a conductive material such as a relatively rigid metal, a pointer ring 72 which is relatively flexible, compressible and deformable (such as a foam or elastomer), a conductive ring 71 which is an electrode made of a relatively flexible metal, another pointer ring 74 which is relatively flexible, compressible and deformable (such as a foam or elastomer), and another conductive ring 75 which is an electrode with an opposite polarity, also made of a relatively flexible metal. When pressure 70A is applied to one side of the ring switch 60a, the tip of the pointer ring 72 is flattened against the rigid center ring 73 which decreases the space between the conductive ring 71 and the center ring 73 and thereby reduces the capacitance in proportion to the pressure 70A as applied. The change in the capacitance between the conductive ring 71 and the center ring 73 activates the handpiece 62, causes the handpiece 62 to run in a specific mode of operation (such as cutting or coagulation), or proportionally increases the power or speed of operation depending on the amount of pressure 70A as applied. Conversely, when pressure 70B is applied to the other side of the ring switch 60a, the tip of the pointer ring 74 is flattened against the rigid center ring 73 which decreases the space between the conductive ring 75 and the center ring 73 and thereby reduces the capacitance in proportion to the pressure 70B as applied. The change in the capacitance between the conductive ring 75 and the center ring 73 activates the handpiece 62, causes the handpiece 62 to run in a specific mode of operation (such as cutting or coagulation), or proportionally decreases the power or speed of operation depending on the amount of pressure 70B as applied.

Figure 7E:
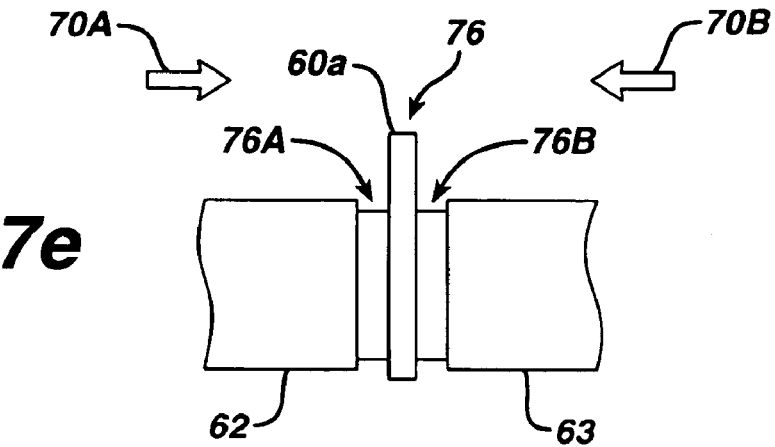
Figure 7F:
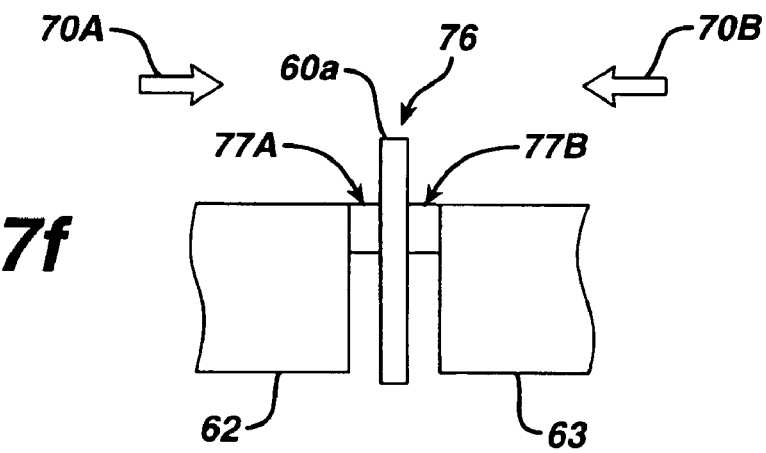

FIGS. 7e and 7f are partial cross sectional views of two other embodiments of the ring switch 60a (taken at B-B of FIG. 6) for the handpiece 62 according to the invention. The ring switch 60a itself is a sensor which comprises a center ring 76 which is made of a relatively rigid material, and two piezo rings 76A (or 77A which is a smaller version of piezo ring 76A) and 76B (or 77B which is a smaller version of piezo ring 76B). When pressure 70A is directly applied against the center ring 76 and indirectly against the piezo ring 76B (or 77B), the ring switch 60a generates an output voltage proportional to the force applied (pressure 70A) and results in a polarity signal, thereby activating the handpiece 62, causing the handpiece 62 to run in a specific mode of operation (such as cutting or coagulation), or proportionally increasing the power or speed of operation depending on the amount of pressure 70A as applied. Conversely, when pressure 70B is directly applied against the center ring 76 and indirectly against the piezo ring 76A (or 77A), the ring switch 60a generates an output voltage proportional to the force applied (pressure 70B) and results in a different or opposing polarity signal, thereby activating the handpiece 62, causing the handpiece 62 to run in a specific mode of operation (such as cutting or coagulation), or proportionally decreasing the power or speed of operation depending on the amount of pressure 70B as applied. This permits at least two modes of operation (such as cutting or coagulation) from a single ring/sensor 60a.

Figure 7G:
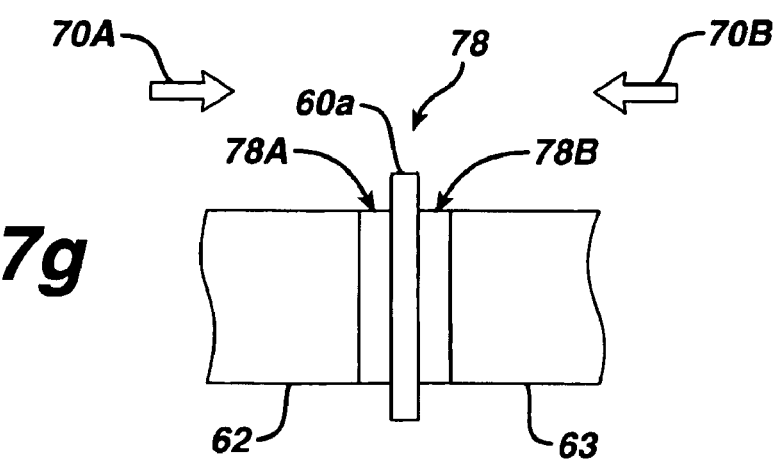

FIG. 7g is a partial cross-sectional view of yet another embodiment of the ring switch 60a (taken at C-C of FIG. 6) for the handpiece 62 according to the invention. According to this particular embodiment, the ring switch 60a includes a single piezo ring 78 with flexible seals 78A and 78B (made of, e.g., elastomer). When pressure 70A is applied against the piezo ring 78, the ring switch 60a generates an output voltage proportional to the force applied (pressure 70A) and results in a polarity signal, thereby activating the handpiece 62, causing the handpiece 62 to run in a specific mode of operation (such as cutting or coagulation), or proportionally increasing the power or speed of operation depending on the amount of pressure 70A as applied. Conversely, when pressure 70B is applied against the piezo ring 78, the ring switch 60a generates an output voltage proportional to the force applied (pressure 70B) and results in an opposing polarity signal, thereby activating the handpiece 62, causing the handpiece 62 to run in a specific mode of operation (such as cutting or coagulation) or proportionally decreasing the power or speed of operation depending on the amount of pressure 70B as applied. In addition, a protective external cover made of elastomer (not shown) may be placed over the ring switch 60a to protect against environmental and impact damage, as in this particular embodiment and other embodiments described herein.

Figure 7H:
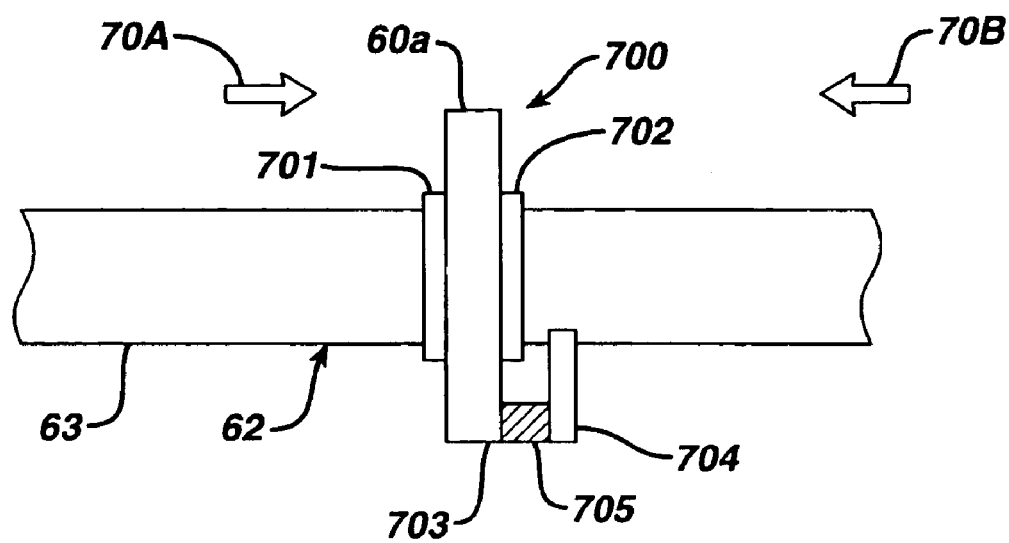

FIG. 7h is a partial cross-sectional view of an additional embodiment of the ring switch 60a (taken at C-C of FIG. 6) for the handpiece 62 according to the invention. According to this particular embodiment, the ring switch 60a includes a center ring 700 which is relatively rigid with two adjacent seals 701 and 702 which are relatively flexible for supporting the center ring 700. Inside the handpiece housing 63, a piezo ring 705 is adhesively attached to the bottom 703 of the center ring 700 with a piezo support ring 704 for supporting the piezo ring 705. When pressure 70A is directly applied against the center ring 700 and indirectly against the piezo ring 705, the ring switch 60*a* generates an output voltage proportional to the force applied (pressure 70A) and results in a polarity signal, thereby activating the handpiece 62 causing the handpiece 62 to run in a specific mode of operation (such as cutting or coagulation), or proportionally increasing the power or speed of operation depending on the amount of pressure 70A as applied. Conversely, when pressure 70B is directly applied against the center ring 700 and indirectly against the piezo ring 705 in the opposite direction, the ring switch 60*a* generates an output voltage proportional to the force applied (pressure 70B) and results in a different or opposing polarity signal, thereby activating the handpiece 62, causing the handpiece 62 to run in a specific mode of operation (such as cutting or coagulation), or proportionally decreasing the power or speed of operation depending on the amount of pressure 70B as applied. Moreover, the center ring 700 can be segmented into two or three sections to particularly localize the pressure applied (70A or 70B) to the corresponding segment of the piezo ring 705. As described herein and above, the piezo ring 705 can also be an integral part of the center ring 700.

Figure 7I:
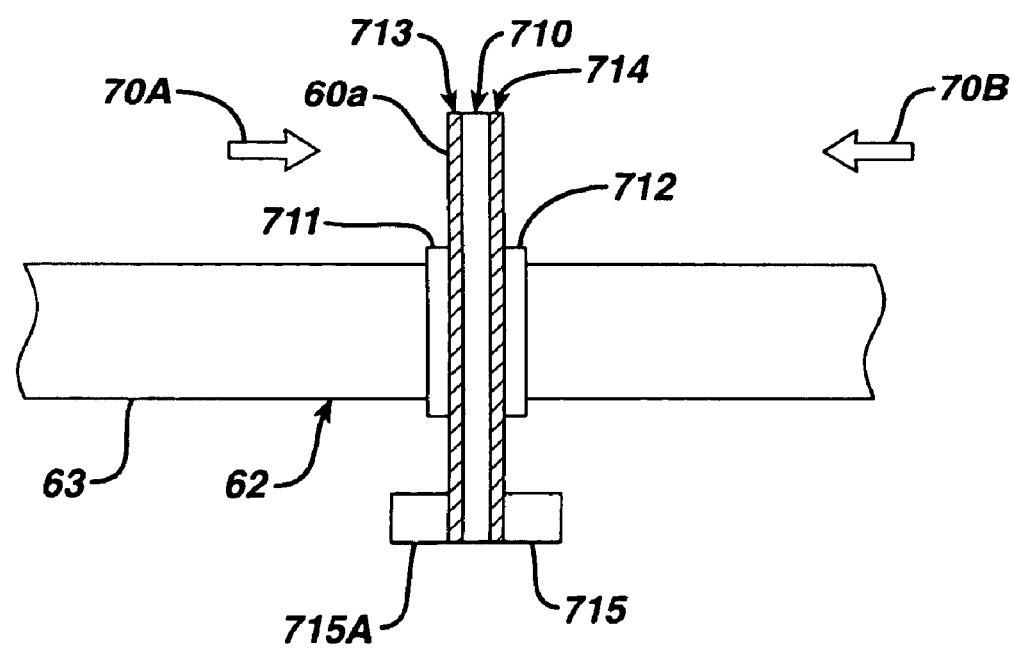

FIG. 7*i* is a partial cross sectional view of another embodiment of the ring switch 60*a* (taken at C-C of FIG. 6) for the handpiece 62 according to the invention. According to this particular embodiment, the ring switch 60*a* includes a center ring 710 made of relatively flexible material, such as foam or elastomer, with two outer rings 713 and 714 which are relatively rigid or semi-rigid, and two relatively flexible rings 711 and 712 for supporting the center ring 710 with the outer rings 713 and 714. Inside the handpiece housing 63, two piezo rings 715A and 715B are fixed to the two sides of the bottom of the center ring 710 with the outer rings 713 and 714. The two piezo rings 715A and 715B are continuously or periodically monitored, i.e., stimulated using AC (alternating current) power near or generally close to the resonant frequency, for avoiding cross talk between the two piezo rings 715A and 715B. The resonant frequency or amount of energy needed to maintain a given displacement is monitored. As pressure (70A or 70B) is applied to the center ring 710, these characteristics change (e.g., the resonant frequency and displacement), and that change is the basis for controlling the mode of operation of the handpiece 62. Alternatively, the pulse, amplitude, echo and timing of the response of the two piezo rings 715A and 715B as a result of the pressure applied (70A and 70B) are monitored, and subsequent Fast Fourier Transform (FFT) analysis can be performed.

When pressure 70A is directly applied against the center ring 710 and indirectly against the piezo rings 715A and 715B, the ring switch 60*a* generates an output voltage proportional to the force applied (pressure 70A) and results in a polarity signal, thereby activating the hand piece 62, causing the handpiece 62 to run in a specific mode of operation (such as cutting or coagulation), or proportionally increasing the speed of operation depending on the amount of pressure 70A as applied. Conversely, when pressure 70B is directly applied against the center ring 710 and indirectly against the piezo rings 715A and 715B in the opposite direction, the ring switch 60*a* generates an output voltage proportional to the force applied (pressure 70B) and results in a different or opposing polarity signal, thereby activating the handpiece 62, causing the handpiece 62 to run in a specific mode of operation (such as cutting or coagulation), or proportionally decreasing the power or speed of operation depending on the amount of pressure 70B as applied.

In the alternative, when pressure 70A is applied to one side of the ring switch 60*a*, the piezo ring 715A is deflected, resulting in a vibration being picked up by the other piezo ring 715B. The center ring 710 which is made of elastomer, is depressed. This increases the vibration transmission to the piezo ring 715B. That change in the vibration transmission activates the handpiece 62, causes the handpiece 62 to run in a specific mode of operation (such as cutting or coagulation), or proportionally increases power or the speed of operation depending on the amount of pressure 70A as applied. Conversely, when pressure 70B is applied to the other side of the ring switch 60*a*, the piezo ring 715B is deflected, resulting in a vibration being picked up by the piezo ring 715A. The center ring 710 is depressed, which increases the vibration transmission to the piezo ring 715A. That change in the vibration transmission deactivates the handpiece 62, causes the handpiece 62, to run in a specific mode of operation (such as cutting or coagulation), or proportionally decreases power or the speed of operation depending on the amount of pressure 70B as applied.

Figure 8:
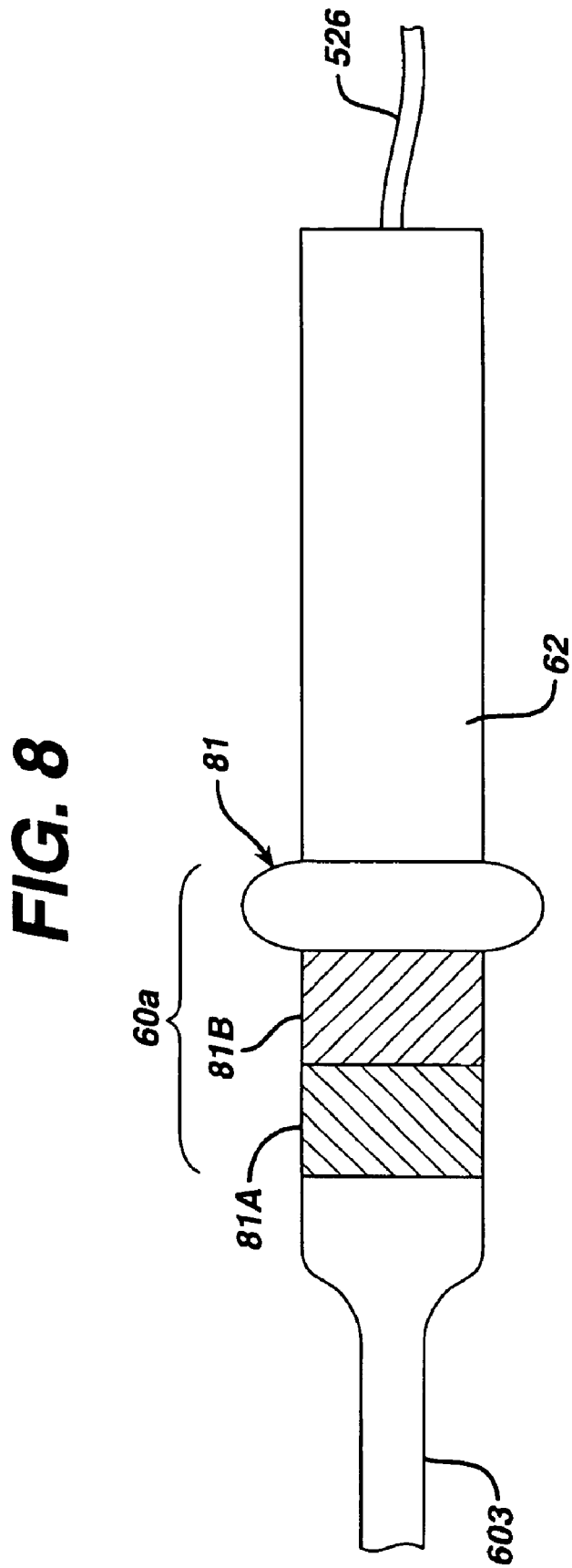
Figure 8A:
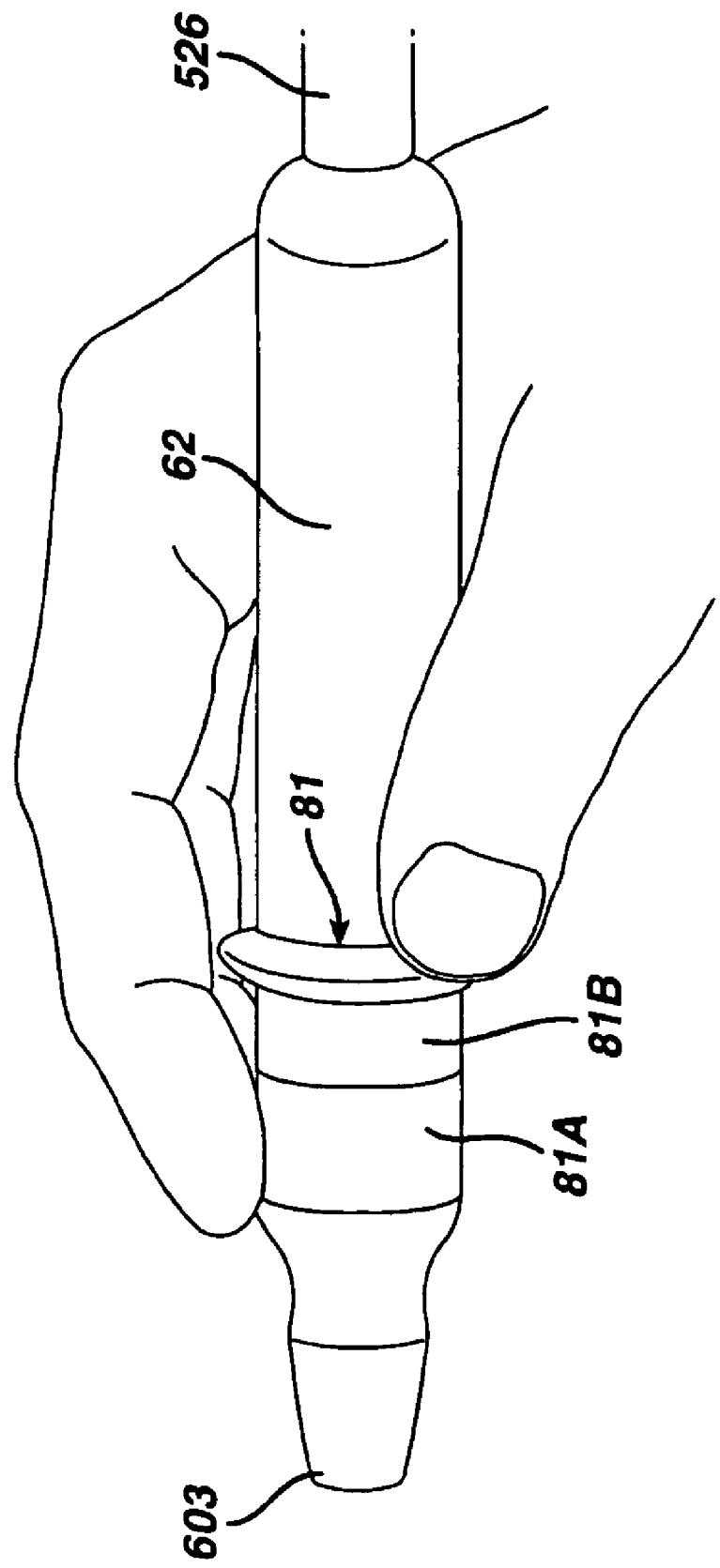

FIGS. 8 and 8*a* are diagrams that respectively illustrate an embodiment and prototype for the ring switch 60*a* with activation zones 81A and 81B for the handpiece 62 according to the invention. A harmonic generator 510, illustrated in FIG. 2, provides electrical energy to the handpiece 62, which imparts ultrasonic longitudinal movement to a surgical device, such as a sharp scalpel blade 603 used for dissection or coagulation: The handpiece 62 is connected to the harmonic generator 510 by a coaxial cable 526. The ring switch 60*a* is a ring-like circumferential appendage on the handpiece 62, including the support ring 81 and two adjacent activation zones 81A and 81B, located near the distal end thereof. The human operators of the handpiece 62 can press their fingers against the surface of the activation zones (81A or 81B) and the finger pressure or force, which can be either perpendicular or non-perpendicular to the surface of the handpiece 62, is sensed and converted into an activation signal. The activation zones 81A and 81B are circumferential bands for sensing pressure for activating and deactivating the handpiece 62, changing the speed thereof (e.g., full or variable power), or running the handpiece 62 in specific modes of operation (e.g., cutting or coagulation). The support ring 81 provides a tactile reference point for a human operator of the handpiece 62 relative to the activation zones 81A and 81B. The support ring 81 also provides finger support for the human operator that reduces inadvertent activation due to unwanted grasping contact with the activation zones 81A and 81B. Furthermore, the support ring 81 can be transparent or translucent for indicating the activation status and mode of operation of the handpiece 62 by becoming illuminated during activation or changing colors according to the current mode of operation.

The activation zones 81A, 81B can include, but are not limited to, (a) force sensitive resistors whose resistance is proportional to the force or pressure applied; (b) force sensitive capacitors whose capacitance is proportional to the pressure, deflection, or compression of the insulation layer between the-two electrodes therein or is proportional to the spacing between the two conductive layers therein; (c) strain gauges mounted underneath or integral with the handpiece housing such that the pressure applied thereto results in an output change of the strain gauges; (d) magnet(s) encased in or resting in an elastomer with a sensor inside the handpiece that detects the field strength of the magnet(s) and monitor changes relative to the force applied or the gap change therein; and (e) piezo film or piezo ceramic elements whose charge or voltage is proportional to the force or pressure applied thereto.

FIGS. 9 and 9*a* are diagrams that respectively illustrate another embodiment of the ring switch 60*a* with segmented activation zones 82A and 82B for the handpiece 62 according to the invention. A harmonic generator 510, illustrated in FIG. 2, provides electrical energy to the handpiece 62 which imparts ultrasonic longitudinal movement to a surgical device such as the sharp scalpel blade 603 used for dissection or coagulation. The handpiece 62 is connected to the harmonic generator 510 by the coaxial cable 526. The ring switch 60*a* is a ring-like circumferential appendage on the handpiece 62, which is segmented into two adjacent activation zones 82A and 82B, located near the distal end thereof. The ring 60*a* is segmented so that action or pressure from one side of the ring (82A) is isolated from the other side of the ring (82B). The segmented activation zones 82A and 82B are for sensing pressure for activating and deactivating the handpiece 62, changing the speed thereof (e.g., full or variable power), or running the handpiece 62 in specific-modes of operation (e.g., cutting or coagulation). For instance, as pressure 70A is applied in one direction against the ring switch 60*a*, one mode of operation is activated, e.g., cutting or variable power, for the handpiece 62. As pressure 70B is applied in the opposite direction against the ring switch 60*a*, another mode of operation is activated, e.g., coagulation or full power, for the handpiece 62. The ring 60*a* itself is a tactile reference point for a human operator of the handpiece 62 relative to the segmented activation zones 82A and 82B. The ring 60*a* also provides finger support for the human operator that reduces inadvertent activation due to unwanted grasping contact with the segmented activation zones 82A and 82B. Furthermore, when pressure 70C is applied to the ring 60*a* in the perpendicular direction, an additional mode of operation is activated. Moreover, the ring 60*a* or the segmented activation zones (82A or 82B) can be transparent or translucent for indicating the activation status and mode of operation of the handpiece 62 by becoming illuminated during activation or changing colors according to the current mode of operation.

FIGS. 10 and 10*a* are diagrams that respectively illustrate another embodiment and prototype for the ring switch 60*a* with activation zones 83A and 83B for the handpiece 62 according to the invention. The harmonic generator 510, illustrated in FIG. 2, provides electrical energy to the handpiece 62 which imparts ultrasonic longitudinal movement to the surgical device 603 used for dissection or coagulation. The handpiece 62 is connected to the harmonic generator 510 by the coaxial cable 526. The ring switch 60*a* is a ring-like circumferential appendage on the handpiece 62, including the distal rib 84, a proximal rib 85, and two adjacent activation zones 83A and 83B therebetween, all located near the distal end of the handpiece 62. Human operators of the handpiece 62 can press their fingers against the surface of the activation zones (83A or 83B) and the finger pressure or force which can be either perpendicular or non-perpendicular to the surface of the handpiece 62, is sensed and converted into an activation signal. The activation zones 83A and 83B are circumferential bands for sensing pressure for activating and deactivating the handpiece 62, changing the speed thereof (e.g., full or variable power), or running the handpiece 62 in specific modes of operation (e.g., cutting or coagulation). The distal rib 84 and the proximal rib 85 provide a tactile reference point for a human operator of the handpiece 62 relative to the activation zones 83A and 83B. The distal rib 84 and the proximal rib 85 are tapered to guide the fingers of the human operator of the handpiece 62 into the activation zones 83A and 83B. The distal rib 84 and the proximal rib 85 also provide finger support for the human operator that reduces inadvertent activation due to unwanted grasping contact with the activation zones 83A and 83B. Furthermore, the distal rib 84 or the proximal rib 85 can be transparent or translucent for indicating the activation status and mode of operation of the handpiece 62 by becoming illuminated during activation or changing colors according to the current mode of operation.

Figure 10B:
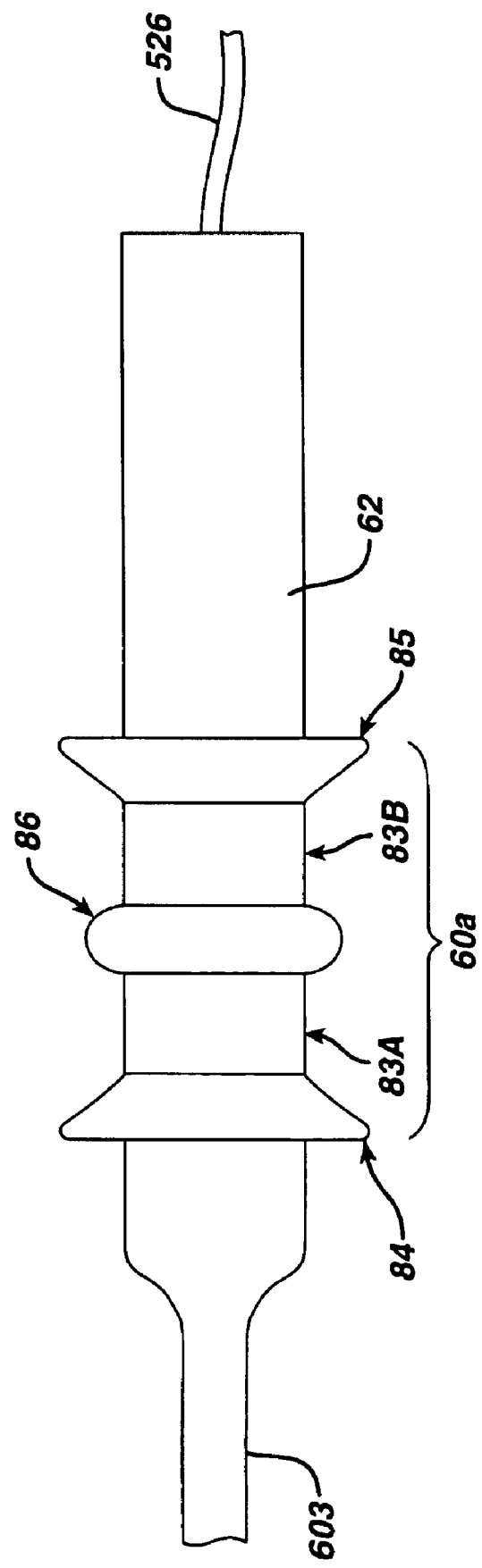

In addition, the ring switch 60*a* can also include a middle rib 86, as shown in FIG. 10*b*, which serves as a divider between activation zones 83A and 83B. The middle rib 86 provides a means for grasping the handpiece 62 in the activation zones without creating undue activation pressure, since the fingers of the human operator bridge across the activation zones 83A and 83B as a result of the addition of the middle rib 86. The middle rib 86 is shaped differently than the distal rib 84 and the proximal rib 85, which provides additional tactile reference feedback for giving the human operator of the handpiece 62 a feel of finger location relative to the active zones 83A and 83B.

FIG. 11 is a diagram that illustrates a further embodiment of the ring switch 60*a* with activation zones 87A and 87B for the handpiece 62 according to the invention. A harmonic generator 510, illustrated in FIG. 2, provides electrical energy to the handpiece 62 which imparts ultrasonic longitudinal movement to a surgical devices such as a sharp scalpel blade 603 used for dissection or coagulation. The handpiece 62 is connected to the harmonic generator 510 by a coaxial cable 526. The ring switch 60*a* is a ring-like circumferential appendage on the handpiece 62, including two activation zones 87A and 87B with a divider 88 which is a recess or protrusion. The human operator of the handpiece 62 can press their fingers against the surface of the activation zones (87A or 87B) and the finger pressure or force, which can be either perpendicular or none perpendicular to the surface of the handpiece 62, is sensed and converted into an activation signal. The activation zones 83A and 83B are circumferential bands for sensing pressure for activating and deactivating the handpiece 62, changing the speed thereof (e.g., full or variable power), or running the handpiece 62 in specific modes of operation (e.g., cutting or coagulation). The divider 88 provides a tactile reference point for a human operator of the handpiece 62 relative to the activation zones 87A and 87B. Furthermore, the divider 88 can be transparent or translucent for indicating the activation status and mode of operation of the handpiece 62 by becoming illuminated during activation or changing colors according to the current mode of operation.

FIG. 12 is a diagram that illustrates an additional embodiment of the ring switch 60*a* with activation zones and sub-zones for the handpiece 62 according to the invention. A harmonic generator 510, illustrated in FIG. 2, provides electrical energy to the handpiece 62 which imparts ultrasonic longitudinal movement to a surgical device such as a sharp scalpel blade 603 used for dissection or coagulation. The handpiece 62 is connected to the harmonic generator 510 by a coaxial cable 526. The ring switch 60*a* is a ring-like circumferential appendage on the handpiece 62, including a sliding barrier 90 and two activation zones 91 and 92 which are tape-like sensors that conform to the handpiece 62. A human operator of the handpiece 62 can press their fingers against the surface activation zones (91 or 92) and this force, which is generally perpendicular to the surface of the handpiece housing, is sensed and converted into an activation signal for activating and deactivating the handpiece 62, or for running it in various modes of operations (e.g., cutting or coagulation). The activation zones 91 and 92 are further divided into two respective groups of sub-zones (91A, 91B, 91C) and (92A, 92B, 92C), which when pressed activate additional modes of operation for the handpiece 62, e.g., variable power levels. The sliding barrier 90 wraps around the handpiece 62 and covers a portion of the activation zones 91 and 92, and more particularly, sub-zones 91A and 92A. The sliding barrier 90 shields sub-zones 91A and 92A to prevent activation, or to attenuate the pressure reaching the particular sub-zone. The sliding barrier 90 can be removably attached to the handpiece 62 which is snapped onto a desired position (e.g., over a particular sub-zone) if needed. The sub-zones allow flexibility of use of the handpiece 62 by providing specific, adaptable configurations of active zones and non-activation finger supporting zones (e.g., 91A and 92A) according to the preferences of the human operator of the handpiece. In addition, the sub-zones can be uniquely colored or numbered or otherwise marked for ready identification by the human operator.

The electro-mechanical switch for the handpiece described herein can be any type, including a conventional mechanical lever contact switch, including, e.g., a stationary contact and a flexible contact. For such a switch, the flexible conductive arm is depressed which makes contact with the stationary contact. An exemplary switch includes a beryllium copper arm that is depressed to make contact with a beryllium copper pad, thereby making contact and completing the switch circuit. The electro-mechanical switch for the handpiece according to the invention can also be a carbon button switch, such as a rubber button that includes a carbon pad attached to the underside of the button. When the button is depressed, the carbon pad descends upon a pair of stationary contacts, such as two gold-plated pads on a printed circuit board. The carbon pad rests against and electrically bridges the gold plated pads, thereby making contact and completing the switch circuit. In a further embodiment, the carbon pad can be replaced with a metallic pad such as a gold-plated copper pad.

Although the invention has been particularly shown and described in detail with reference to the preferred embodiments thereof, the embodiments are not intended to be exhaustive or to limit the invention to the precise forms disclosed herein. It will be understood by those skilled in the art that many modifications in form and detail may be made without departing from the spirit and scope of the invention. Similarly, any process steps described herein may be interchangeable with other steps to achieve substantially the same result. All such modifications are intended to be encompassed within the scope of the invention, which is defined by the following claims and their equivalents.

We claim:

1. A method for controlling an ultrasonic surgical instrument, comprising the steps of:
   obtaining a housing having a transducer for converting electrical energy to mechanical energy, at least one switch located on the housing, a sensor for outputting a variable pressure value based on a user applied pressure to the at least one switch and a generator for outputting a variable power level to energize the transducer;
   monitoring the user applied pressure to the switch and outputting a pressure value in response thereto;
   activating the transducer at a first power level if the monitored user applied pressure reaches a first threshold;
   deactivating the transducer if the monitored user applied pressure reaches a second threshold;
   providing a switching functionality according to a lagging effect as the monitored user applied pressured is changed; and
   operating the transducer at a variable power level in response to the user applied monitored pressure.

2. The method of claim 1 further comprising the step of operating the transducer at a power level selected from a plurality of power levels if the user applied monitored pressure reaches a specific threshold of a respective plurality of thresholds corresponding to the plurality of power levels.

3. The method of claim 1 wherein the sensor is selected from a group consisting of an electro-mechanical switch, a force-sensitive resistor, force sensitive capacitor, strain gauge, magnet, ferromagnet, piezo film and piezo ceramic.

4. The method of claim 1 wherein the switch is generally aligned with a blade as the blade is rotated.

5. The method of claim 1 wherein the generator is located within a console having a display for indicating the power level.

6. A method for controlling an ultrasonic surgical instrument, comprising the steps of:
   obtaining a housing having a transducer for converting electrical energy to mechanical energy, at least one switch located on the housing, a sensor for outputting a variable pressure value based on a user applied pressure to the at least one switch and a generator for outputting a variable power level to energize the transducer;
   monitoring a user applied pressure to the switch and outputting a pressure value in response thereto;
   activating the transducer at a first power level if the monitored user applied pressure reaches a first threshold;
   deactivating the transducer if the monitored user applied pressure reaches a second threshold; and
   operating the transducer at a variable power level in response to the user applied monitored pressure.

* * * * *